US007112574B2

(12) United States Patent
Van Tilburg et al.

(10) Patent No.: US 7,112,574 B2
(45) Date of Patent: Sep. 26, 2006

(54) C2,8-DISUBSTITUTED ADENOSINE DERIVATIVES AND THEIR DIFFERENT USES

(75) Inventors: Erica Van Tilburg, Amsterdam (NL); Ad Ijzerman, Haarlem (NL)

(73) Assignees: Universiteit Leiden, Leiden (NL); Can-Fite Biopharma Ltd., Petach Tikva (IL)

( * ) Notice: Subject to any disclaimer, the term of this patent is extended or adjusted under 35 U.S.C. 154(b) by 136 days.

(21) Appl. No.: 10/469,645

(22) PCT Filed: Mar. 3, 2002

(86) PCT No.: PCT/IL02/00161

§ 371 (c)(1),
(2), (4) Date: Feb. 9, 2004

(87) PCT Pub. No.: WO02/070534

PCT Pub. Date: Sep. 12, 2002

(65) Prior Publication Data

US 2004/0116374 A1 Jun. 17, 2004

(30) Foreign Application Priority Data

Mar. 3, 2001 (GB) ................. 0105335.4

(51) Int. Cl.
*A61K 31/70* (2006.01)
*C07H 19/167* (2006.01)
(52) U.S. Cl. .................. 514/46; 536/27.61; 536/27.63; 536/27.7
(58) Field of Classification Search ................. 514/46; 536/27.61, 27.63, 27.7
See application file for complete search history.

(56) References Cited

U.S. PATENT DOCUMENTS

| 3,968,102 | A | | 7/1976 | Suehiro et al. | |
|---|---|---|---|---|---|
| 5,189,027 | A | * | 2/1993 | Miyashita et al. | 514/46 |
| 5,278,150 | A | * | 1/1994 | Olsson et al. | 514/46 |
| 5,877,180 | A | * | 3/1999 | Linden et al. | 514/45 |
| 5,998,423 | A | * | 12/1999 | Manneth et al. | 514/265.1 |
| 6,407,076 | B1 | * | 6/2002 | Box et al. | 514/46 |
| 6,448,235 | B1 | * | 9/2002 | Linden et al. | 514/46 |
| 6,514,949 | B1 | * | 2/2003 | Linden et al. | 514/46 |
| 6,576,620 | B1 | * | 6/2003 | Belardinelli et al. | 514/46 |
| 6,605,597 | B1 | * | 8/2003 | Zablocki et al. | 514/46 |

FOREIGN PATENT DOCUMENTS

| WO | WO 00/72799 A2 * | 12/2000 |
|---|---|---|
| WO | WO00/72799 A2 * | 12/2000 |
| WO | WO 00/78777 A1 | 12/2000 |

OTHER PUBLICATIONS (V) Niedzwicki et al., "Structure-Activity Relationship of Ligands of Human Plasma Adenosine Deaminase2," Biochemical Pharmacology, 41(11), 1615-1624 (Jun. 1, 1991).*
(W) Zady et al., "Kinetics and Mechanism of Carbon-8 Methylation of Purine Bases and Nucleosides by Methyl Radicals," Journal American Chemical Society, 99(15), 5096-5101 (Jul. 20, 1977).*
(X) Fujita et al., "Antiviral Activity of 2-Aminoadenosine, 2-Aminodeoxyadenosine and Their N6-Substituted Derivatives in Vero Cells," Oyo Yakuri, 49(6), 627-634 (1995).*
(R)van Tilburg et al., "N6,5'-Disubstituted Adenosine Derivatives as Partial Agonists for the Humans Adenosine A3 Receptor," Journal of Medicinal Chemistry, 42(8), 1393-1400 (1999); Web published Mar. 31, 1999.*
(S) Kanaya et al., "Poly(2-amino-8-methyldeoxyadenylic acid): Contrasting Effects in Deoxy- and Ribopolynucleotides of 2-Amino and 8-Methyl Substituents," Biochemistry, 26(22), 7159-7165 (1987).*
(T) Marumoto et al., "A New Method for Synthesis of Nucleoside 3',5'-Cyclic Phosphates. Cyclization of Nucleoside 5'-Trichloromethylphosphonates," □□Chemical & Pharmaceutical Bulletin, 23(10), 2295-2300 (Oct. 1975).*
(U) Ikehara et al., "Studies of Nucleosides and Nucleotides. LXXXI. Synthesis and Characterization of 8-Methyladenosine," □□Chemical & Pharmaceutical Bulletin, 25(10), 2702-2707 (Oct. 1977).*
(V) Niedzwicki et al., "Structure-Activity Relationship of Ligands of Human Plasma Adenosine Deaminase2," Biochemical Pharmacology, 41(11), 1615-1624 (Jun. 1, 1991).*
(W) Zady et al., "Kinetics and Mechanism of Carbon-8 Methylation of Purine Bases and Nucleosides by Methyl Radicals," Journal American Chemical Society, 99(15), 5096-5101 (Jul. 20, 1977).*
(X) Fujita et al., "Antiviral Activity of 2-Aminoadenosine, 2-Aminodeoxyadenosine and Their N6-Substituted Derivatives in Vero Cells," Oyo Yakuri, 49(6), 627-634 (1995).*
van Tilburg et al., "$N^6$,5'-Disubstituted Adenosine Derivatives as Partial Agonists for the Humans Adenosine $A_3$ Receptor," *Journal of Medicinal Chemistry*, 42(8), 1393-1400 (1999); Web published Mar. 31, 1999.*

(Continued)

*Primary Examiner*—S. Anna Jiang
*Assistant Examiner*—L. E. Crane
(74) *Attorney, Agent, or Firm*—Browdy and Neimark, PLLC

(57) ABSTRACT

Novel C2,8-disubstituted adenosine derivatives disclosed herein have been found to be potent adenosine receptor agonists, in particular for the A2A receptor. The said compounds have biological activity against conditions such as hypertension, ischemic heart disease, ischemic brain disease, psychosis and wound healing. Further, the invention also discloses a process for the preparation of such compounds and pharmaceutical compositions comprising them.

25 Claims, No Drawings

OTHER PUBLICATIONS

Kanaya et al., "Poly(2-amino-8-methyldeoxyadenylic acid): Contrasting Effects in Deoxy- and Ribopolynucleotides of 2-Amino and 8-Methyl Substituents," *Biochemistry*, 26(22), 7159-7165 (1987).*

Marumoto et al., "A New Method for Synthesis of Nucleoside 3',5'-Cyclic Phosphates. Cyclization of Nucleoside 5'-Trichloromethylphosphonates," *Chemical & Pharmaceutical Bulletin*, 23(10), 2295-2300 (Oct. 1975).*

Ikehara et al., "Studies of Nucleosides and Nucleotides. LXXXI. Synthesis and Characterization of 8-Methyladenosine," *Chemical & Pharmaceutical Bulletin*, 25(10), 2702-2707 (Oct. 1977).*

Niedzwicki et al., "Structure-Activity Relationship of Ligands of Human Plasma Adenosine Deaminase$_2$," *Biochemical Pharmacology*, 41(11), 1615-1624 (Jun. 1, 1991).*

Zady et al., "Kinetics and Mechanism of Carbon-8 Methylation of Purine Bases and Nucleosides by Methyl Radicals," *Journal American Chemical Society*, 99(15), 5096-5101 (Jul. 20, 1977).*

Fujita et al., "Antiviral Activity of 2-Aminoadenosine, 2-Aminodeoxyadenosine and Their $N^6$-Substituted Derivatives in Vero Cells," *Oyo Yakuri*, 49(6), 627-634 (1995).*

Chemical Abstract No. 84:17662 & Marumoto et al., Chem.Pharm. Bull., (1975), 23(10), 2295-2300. See abstract and compound with registry No. 57627-54-0, (Chem. Abstr., 1976).

Chemical Abstract No. 87: 136271 & Zady et al, J. Am. Chem. Soc., (1977), 99(15), 5096-5101. See abstract and compound with registry No. 63954-66-5, (Chem. Abstr., 1977).

Chemical Abstract No. 88: 121631 & Ikehara et al., Chem. Pharm. Bull. (1977), 25(10), 2702-2707. See abstract and compound with registry No. 65991-09-5, (Chem. Abstr, 1978).

Chemical Abstract No. 107: 193251 & Kanaya et al., Biochemistry. (1987), 26(22), 7159-7165. See abstract and compound with registry No. 80326-50-7, (Chem. Abstr., 1987).

Chemical Abstract No. 114: 207670 & Ratsep et al., Nucleosides & Nucleotides, (1990), 9(8), 1001-1013. See abstract and compound with registry No. 133502-38-2, (Chem. Abstr., 1991).

Chemical Abstract No. 115: 67360 & Niedzwicki et al., Biochem. Pharmacol, (1991), 41(11), 1615-1624. See abstract and compound with registry No. 7502-60-7, (Chem. Abstr., 1991).

Chemical Abstract No. 123: 47455 & Fujita et al., Oyo Yakuri, (1995), 49(6), pp. 627-634. See abstract, (Chem. Abstr., 1995).

Camaioni, et al., "Adenosine Receptor Agonists: Synthesis and Biological Evaluation of the Diastereoisomers of 2-(3-Hydroxy-3-phenyl-1-propyn-1-yl)NECA", Bioorganic & Medicinal Chemistry. 1997, vol. 5 No. 12, 2267- 2275.

Cristalli, et al., "2-Alkynyl Derivatives of Adenosine and Adenosine-5'-N-ethyluronamide as Selective Agonists at $A_2$ Adenosine Receptors", J. Med. Chem. 1992, vol. 35, 2363-2368, (Issue No. 13).

Francis, et al., "Highly Selective Adenosine $A_2$ Receptor Agonists in a Series of N-Alkylated 2-Aminoadenosines", J. Med Chem. 1991, vol. 34, 2570-2579, (Issue No. 8).

Homma, et al., "Nucleosides and Nucleotides. 112. 2-(1-Hexyn-1-yl)adenosine-5'-uroamides: A New Entry of Selective $A_2$ Adenosine Receptor Agoinists with Potent Antigypertensive Activity," J. Med. Chem. 1992, vol. 35, 2881-2890, (Issue No. 15).

Klotz, et al., "2-Substituted N-ethylcarboxamidoadenosine Derivatives as High-affinity Agonists at Human $A_3$ Adenosine Receptors", Naunyn-Schmiedeberg's Arch Pharmacol. 1999, vol. 360, 103-108.

Matsuda, et a:., "Palladium-catalyzed Cross-Coupling of 2-Iodoadenosine with Terminal Alkynes: Synthesis and Biological Activities of 2-Alkynyladenosines", Chem. Pharm. Bull. 1985, vol. 33(4), 1766-1769.

Matsuda, et al., "Nucleosides and Nucleotides. 103. 2-Alkynyladenosines: A Novel Class of Selective Adenosine $A_2$ Receptor Agonists with Potent Antihypertensive Effects", J. Med. Chem. 1992, vol. 35, 241-252, (Issue No. 2; Jan. 24, 1992).

Ratsep, et al., "8-Diazoguanosine, 2,8-Diaminoadenosine and Other Purine Nucleosides Derived from Guanosine", Nucleosides & Nucleotides. 1990, vol. 9 (8), 1001-1013.

Roelen, et al., "$N^6$, C8-Disubstituted Adenosine Derivatives as Partial Agonists for Adenosine $A_1$ Receptors", J. Med. Chem. 1996, vol. 39, 1463-1471, (Issue No. 7; Mar. 29, 1996).

Vittori, et a;., "2-Alkenyl and 2-Alkyl Derivatives of Adenosine and Adenosine-5'-N-Ethyluronamide: Different Affinity and Selectivity of E-and Z-Diastereomers at $A_{2A}$ Adenosine Receptors", J. Med. Chem. 1996, vol. 39, 4211-4217, (Issue No. 21).

Vittori, et al., "Synthesis and Receptor Affinity of Polysubstituted Adenosines", Nucleosides & Nucleotides. 1999, vol. 18(4&5), 739-740.

Volpini, et al., "Synthesis of Di-and Tri-substituted Adenosine Derivatives and Their Affinities at Human Adenosine Receptor Subtypes", Nucleosides & Nucleotides. 1999, 18(11&12), 2511-2520.

* cited by examiner

C2,8-DISUBSTITUTED ADENOSINE DERIVATIVES AND THEIR DIFFERENT USES

CROSS-REFERENCE TO RELATED APPLCIATIONS

This application is a 371 national stage application of PCT International application PCT/IL02/00161, filed Mar. 3, 2002.

FIELD OF THE INVENTION

The present invention relates to novel C2,8-disubstituted adenosine derivatives, their process of preparation and different uses.

BACKGROUND OF THE INVENTION

Adenosine mediates a wide variety of effects as a result of its activation of specific membrane-bound receptors called $P_1$-purinoceptors. The three subclasses of $P_1$-purinoceptors are $A_1$, $A_2$ and $A_3$, with $A_2$ further subdivided into $A_{2A}$ and $A_{2B}$. All adenosine receptors are coupled to the enzyme adenylate cyclase; activation of the $A_1$ and $A_3$ adenosine receptors inhibit the adenylate cyclase, whereas activated $A_{2A}$ and $A_{2B}$ receptors stimulate it. The adenosine $A_{2A}$ receptor can be found throughout the whole body, and $A_{2A}$ receptor agonists might be used to inhibit platelet aggregation in thrombosis, in the diagnosis of diseases in coronary arteries, in ischemia and reperfusion.[1] Furthermore, activation of adenosine $A_{2A}$ receptors has been shown to alter the binding characteristics of other receptors. Stimulation of adenosine $A_{2A}$ receptors in rat striatal membranes reduces the affinity of agonist binding to dopamine $D_2$ receptors.[2,3] This raises the possibility of using adenosine $A_{2A}$ receptor agonists as a novel therapeutic approach in the treatment of psychosis. However, these desired actions of agonists for the adenosine $A_{2A}$ receptor may be accompanied with serious side effects such as cardiovascular actions, since the receptor is ubiquitously distributed. The design of partial agonists for the adenosine receptors has already been shown to be a useful tool to achieve selectivity of action in vivo by exploitation of the differences in receptor-effector coupling in various tissues.[4-7] Hence, partial agonists for the adenosine $A_{2A}$ receptor might then be developed as antipsychotic agents also devoid of undesired cardiovascular actions.

Selectivity for the adenosine $A_{2A}$ receptor can be obtained by the introduction of a C2-substituent, such as a 1-hexynyl or a 1-hexenyl group that have been shown to induce high affinity for the adenosine $A_{2A}$ receptor compared to $A_1$.[8-10] Partial agonism for adenosine receptors in general has been achieved by the introduction of alkylthio-substituents at the 5'-position.[5,11] However, partial agonism for the adenosine $A_1$ receptor has also successfully been accomplished by introducing alkylamino substituents at the C8-position of adenosine.[12] 8-Alkylamino substituted CPA derivatives have proven to be adenosine $A_1$ receptor partial agonists in vivo when assessed for cardiovascular activity, although with modest affinities.[6,13,14]

LIST OF PRIOR ART

The following is a list of prior art which is considered to be pertinent for describing the state of the art in the field of the invention, all of which are also included in the list of publication provided hereinafter. Acknowledgement of these references herein will be made by indicating the number from the said list list of publications which is also indicated in brackets hereinbelow.

Cristalli, G., Eleuteri, A., Vittori, S., Volpini, R, Lohse, M. J., Klotz, K.-N., *J. Med. Chem.*, 1992, 35, 2363–2368 (reference no. 8).

Matsuda, A., Shinozaki, M., Yamaguchi, T., Homma, H., Nomoto, R., Miyasaka, T., Watanabe, Y., Abiru, T., *J. Med. Chem.*, 1992, 35, 241–252 (reference no. 9).

Vittori, S., Camaioni, E., Di Francesco, E., Volpini, R., Monopoli, A., Dionisotti, S., Ongini, E., Cristalli, G., *J. Med. Chem.*, 1996, 39, 4211–4217 (reference no. 10).

Matsuda, A., Shinozaki, M., Miyasaka, T., Machida, H., Abiru, T., *Chem. Pharm. Bull.*, 1985, 33, 1766–1769 (reference no. 15).

Francis, J. E., Webb, R. L., Ghai, G. R., Hutchison, A. J., Moskal, M. A., deJesus, R., Yokoyama, R., Rovinski, S. L., Contardo, N., Dotson, R., Barclay, B., Stone, G. A., Jarvis, M. F., *J. Med. Chem.*, 1991, 34, 2570–2579 (reference no. 20).

Camaioni; E., DiFrancesco, E., Viffori, S., Volpini, R., Cristalli, G., *Bioorg. Med. Chem.*, 1997, 5, 2267–2275 (reference no. 22).

Homma, H., Watanabe, Y., Abiru, T., Murayama, T., Nomura, Y., Matsuda, A. *J. Med. Chem.*, 1992, 35, 2881–2890 (reference no. 23).

Vittori, S., Camaioni, E., Constanzi, S., Volpini, R., Klotz, K.-N., Cristalli, G., *Nucleosides and Nucleotides*, 1999, 18, 739–740 (reference no. 24).

Volpini, R., Camaioni, E., Costanzi, S., Vittori, S., Klotz, K.-N., Cristalli, G., *Nucleosides and Nucleotides*, 1999, 18, 2511–2520 (reference no. 25).

Klotz, K.-N., Camaioni, E., Volpini, R, Kachler, S., Vittori, S., Cristalli, G., *Naunyn-Schmiedeberg's Arch. Pharmacol.*, 1999, 360, 103–108 (reference no. 26).

SUMMARY OF THE INVENTION

According to the first aspect, the present invention provides C2,8-di-substituted adenosine derivatives having the following general formula (I) (hereinafter referred to at times as the "the compound of the present invention"):

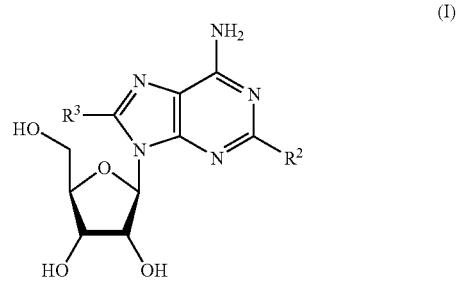

wherein $R^2$ and $R^3$ which may be the same or different, represent a lower alkyl, lower alkenyl, lower alkynyl, lower (ar)alkyl, lower alkoxy, lower alkylidenehydrazino group, cyano, acetoamino, halogen, a group of the general formula —$NR^4R^5$ wherein $R^4$ and $R^5$ represent, independently, a hydrogen atom, lower alkyl or (ar) alkyl group or a group of the general formula —$SR^6$, wherein $R^6$ represents a hydrogen, lower alkyl, lower alkanoyl or (ar)alkyl groups, or a salt of the above compound, with the provisos that:
(i) when $R^2$ represents —$NH_2$, $R^3$ does not represent a halogen, alkyl or alkoxy;
(ii) when $R^2$ represents an alkythio, $R^3$ does not represent an alkyl;
(iii) when $R^2$ represents a halogen or alkyl, $R^3$ does not represent, respectively, a halogen or alkyl.

The term "lower alkyl" as used herein refers to any saturated carbohydrate, either linear or branched chain comprising from one to ten carbon atoms in the backbone of the carbohydrate.

Accordingly, the terms "lower alkenyl" and "lower alkynyl" refer to a linear or branched carbohydrate comprising from two to ten carbon atoms in the backbone, wherein at least two of the carbon atoms are connected via a double or triple bond, respectively.

Thus, it is to be understood that the term "lower" when used for defining a carbohydrate, refers to any carbohydrate chain having no more than 10 carbon atoms.

The compound of the invention also includes salts of the compound of formula (I) and in particular, physiologically acceptable salts. The term "physiologically acceptable salt" refers to any non-toxic alkali metal, alkaline earth metal, and ammonium salts commonly used in the pharmaceutical industry, including the sodium, potassium, lithium, calcium, magnesium, barium ammonium and protamine zinc salts, which are prepared by methods known in the art. The term also includes non-toxic acid addition salts, which are generally prepared by reacting the compounds of this invention with a suitable organic or inorganic acid. The acid addition salts are those which retain the biological effectiveness and properties of the free bases and which are not biologically or otherwise undesirable. Examples include acids are those derived from mineral acids, and include, inter aila, hydrochloric, hydrobromic, sulfuric, nitric, phosphoric, metaphosphoric and the like. Organic acids include, inter alia, tartaric, acetic, propionic, citric, malic, malonic, lactic, fumaric, benzoic, cinnamic, mandelic, glycolic, gluconic, pyruvic, succinic salicylic and arylsulphonic, e.g. p-toluenesulphonic, acids.

The present invention also provides a process for the preparation of the compound of the present invention (i.e. the compound of formula (I) as defined above) or a salt thereof, the process comprising in general treating a compound of the formula (II):

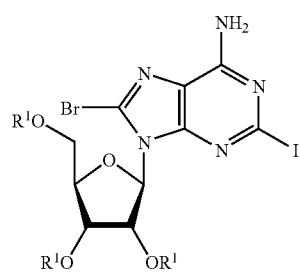

wherein
$R^1$ represents a hydrogen atom or methylcarbonyl group;
with one or more equivalents of at least one reagent selected from:
$PdCl_2$, triaryl phosphate, CuI and an (ar)alkyn;
tetrakis(triphenylphosphine)-palladium(0), $K_2CO_3$ and (E)-1-borocatechol-1-(ar)alkene, or a nucleophile containing an $R^3$ group as defined below;
to obtain said compound of general formula (I).

As will be described in detail hereinafter, the process of the present invention may provide a compound wherein $R^2$ and are $R^3$ are the same or different, depending on the amount and number of reagents employed. For example, in order to obtain different substituents at the 2- and 8-positions of the compound of general formula (I), the process is preferably carried out in two steps, each step comprising treatment with 1 equivalent of one of said reagents carrying different substituents.

The invention also provides pharmaceutical compositions comprising as active ingredient an effective amount of one or more of the compounds of the invention as defined hereinbefore.

Evidently, any other use of the novel compounds and compositions disclosed herein are within the scope of the present invention.

DETAILED DESCRIPTION OF THE INVENTION

The present invention is based on the surprising finding that C8-substituted and C2,8-disubstituted adenosine derivatives display higher adenosine $A_{2A}$ receptor affinity and/or $A_{2A}$ selectivity compared to the $A_1$ and $A_3$ receptors.

According to a first aspect, the present invention provides C2,8-disubstituted adenosine derivatives having the following general formula (I):

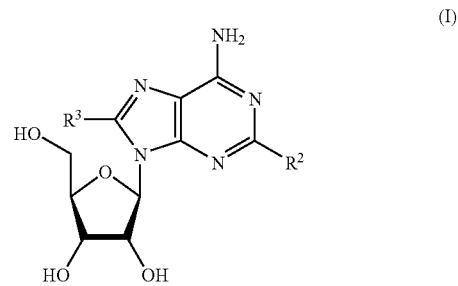

wherein
$R^2$ and $R^3$, which may be the same or different, represent a lower alkyl, lower alkenyl, lower alkynyl, lower aralkyl, lower alkoxy, lower alkylidenehydrazino, cyano, acetoamino, halogen, a group of the general formula —$NR^4R^5$ wherein $R^4$ and $R^5$ represent, independently, a hydrogen atom, lower alkyl or (ar)alkyl or a group of the general formula —$SR^6$, wherein $R^6$ represents a hydrogen, lower alkyl, lower alkanoyl or (ar)alkyl;
or a salt of the above compound, with the provisos that:
(i) when $R^2$ represents —$NH_2$, $R^3$ does not represent a halogen, allyl or alkoxy;
(ii) when $R^2$ represents an alkylthio, $R^3$ does not represent an alkyl;
(iii) when $R^2$ represents a halogen or alkyl, $R^3$ does not represent, respectively, a halogen or alkyl.

According to one embodiment, the substituent $R^2$ represents a halogen atom, a $C_2$–$C_{10}$ alkenyl or $C_2$–$C_{10}$ alkynyl or (ar)alkylamine. More preferably, the alkenyl or alkynyl groups are, respectively $C_6$-alkenyl or $C_6$-alkynyl, the halogen atom is iodine and the (ar)alkylamine group is benzylamine.

According to one more specific embodiment, $R^2$ is a halogen atom, preferably an iodine atom.

According to another specific embodiment, $R^2$ is 1-hexenyl or 1-hexynyl, the former preferably representing the (E) 1-hexenyl isomer.

The $R^3$ substituent preferably represents an alkylamine, aralkylamine, alkynyl or alkynyl group. The alkylamine is preferably selected from methylamine, ethylamine, propylamine, butylamine, the alkynyl is prefereably 1-hexynyl, and the (ar)alkylamine is preferebly benzylamine, however, the latter may also include anilines and substituted arylamines.

As will be detailed in the following specific examples, it has been found that the compounds of the present invention are biologically active.

The term "biologically active" indicates that the compound of the present invention has some sort of a biological activity, for example, a measurable effect on a target receptor. As will be detailed hereinafter, the compound of the present invention may induce adenosine receptor activity, preferably acting as adenosine receptor agonists and more preferably as adenosine $A_{2A}$ receptor agonists.

The term "agonist" refers to a biologically active ligand, which binds to its complementary biologically (active) receptor and activates the latter either to cause a biological response in the receptor or to enhance preexisting biological activity of the receptor. The agonist in fact mimics the effect of the natural ligand, in the present case, adenosine, or at times, even increases or prolongs the duration of the biological effect obtained as compared to the effect induced by the natural ligand.

The compounds of the present invention were specifically found to activate adenosine receptors, with a higher selectivity and affinity for the adenosine $A_{2A}$ receptor. Thus, the compounds of the present invention may be recognized as adenosine $A_{2A}$ receptor agonists. More preferably and as will be shown in the following Specific Examples, the compounds of the present invention are partial agonists of the adenosine $A_{2A}$ receptor.

receptor if it produces (or induces (e.g. when increased in concentration) the maximal possible response achievable by activation of this receptor.

A compound according to the invention is considered a "partial agonist" if it is unable to produce maximal activation of the receptor to which it binds no matter how high is its concentration.

Preferred compounds according to the present invention include:
2-iodo-8-methylaminoadenosine (compound 7 hereinafter);
2-iodo-8-ethylaminoadenosine (compound 8 hereinafter);
2-iodo-8-propylaminoadenosine (compound 9 hereinafter);
2-iodo-8-butylaminoadenosine (compound 10 hereinafter);
2-iodo-8-benzylaminoadenosine (compound 11 hereinafter);
2-(1-hexynyl)-8-methylaminoadenosine (compound 12 hereinafter);
2-(1-hexynyl)-8-ethylaminoadenosine (compound 13 hereinafter);
2-(1-hexynyl)-8-propylaminoadenosine (compound 14 hereinafter);
2-(1-hexynyl)-8-butylaminodenosine (compound 15 hereinafter);
2-(1-hexynyl)-8-benzylaminoadenosine (compound 16 hereinafter);
2-((E)-1-hexenyl)-8-methylaminoadenosine (compound 17 hereinafter);
2-((E)-1-hexenyl)-8-ethylaminoadenosine (compound 18 hereinafter);
2-((E)-1-hexenyl)-8-propylaminoadenosine (compound 19 hereinafter);
2-((E)-1-hexenyl)-8-butylaminoadenosine (compound 20 hereinafter);
2-((E)-1-hexenyl)-8-benzylaminoadenosine (compound 21 hereinafter);
2,8-di-(1-hexynyl)adenosine (compound 22 hereinafter);
2,8-di-benzylaminoadenosine (compound 23 hereinafter);

By a second of its aspects, the present invention provides a process for the preparation of a compound of the general formula (I):

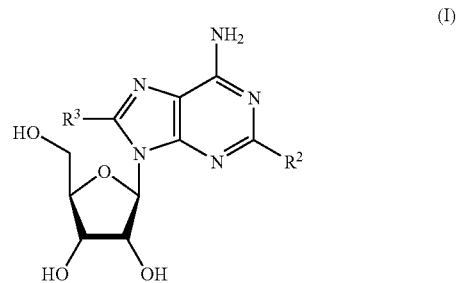

(I)

in which
$R^2$ and $R^3$ which may be the same or different, represent a lower alkyl, lower alkenyl, lower alkynyl, lower (ar)alkyl, lower alkoxy, lower alkylidenehydrazino, cyano, acetoamino, halogen, a group of the general formula $—NR^4R^5$ wherein $R^4$ and $R^5$ represent, independently, a hydrogen atom, lower allyl or aralkyl group or a group of the general formula $—SR^6$, wherein $R^6$ represents a hydrogen, lower alkyl, lower alkanoyl or (ar)alkyl groups, or a salt of said compound, with the provisos that:
(i) when $R^2$ represents $—NH_2$, $R^3$ does not represent a halogen, alkyl or alkoxy;
(ii) when $R^2$ represents an alkylthio, $R^3$ does not represent an alkyl;
(iii) when $R^2$ represents a halogen or alkyl, $R^3$ does not represent, respectively, a halogen or alkyl;

the process comprises treating a compound of the general formula (II):

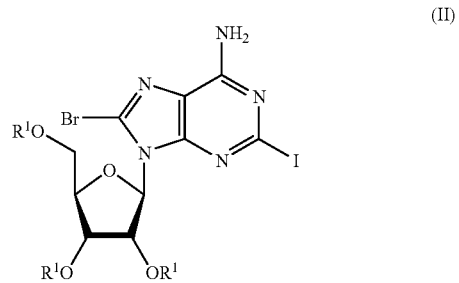

(II)

wherein
$R^1$ represents a hydrogen atom or methylcarbonyl group; with one or more equivalents of at least one reagent selected from:
  $PdCl_2$, triaryl phosphate, CuI and an (ar)alkyn; and/or
  tetrakis(triphenylphosphine)palladium(0), $K_2CO_3$ and (E)-1-borocatechol-1-(ar)alkene, and/or
  a nucleophile containing an $R^3$ group as defined above.

The process of the invention may be carried out in a single step reaction, according to which two or more equivalents of the reagent selected are applied on the starting compound, or in two steps.

When performing the reaction in a single step, the resulting compound may contain the same or different substituents in $R^2$ and $R^3$ depending on the amount of reagent employed. For example, when using only one equivalent of the reagent, a compound of the following general formula (III) is obtained in which only C8 is substituted, while when using two or more equivalents of the reagent a compound in which C2 and C8 are substituted with the same group is obtained.

When carrying out the process in two steps, it is possible to obtain a product in which $R^2$ and $R^3$ are different. To this end, the two sequential reactions steps employ each about one equivalent of different reagents selected from:

PdCl$_2$, triaryl phosphate, CuI and an (ar)alkyn; or
tetrakis(triphenylphosphine)-palladium(0), K$_2$CO$_3$ and (E)-1-borocatechol-1-(ar)alkene, or
a nucleophile containing an $R^3$ group as defined;

As an intermediate product, i.e. after applying one equivalent of the reagent, a compound of the following general formula (III) is obtained:

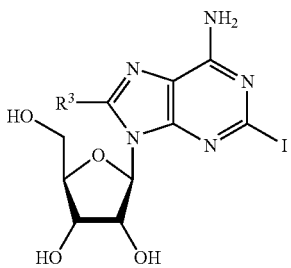

(III)

in which $R^3$ is as defined, which is then further reacted with one equivalent of a reagent selected from:

PdCl$_2$, triaryl phosphate, CuI and an (ar)allyn; or
tetrakis(triphenylphosphine)-palladium(0), K$_2$CO$_3$ and (E)-1-borocatechol-1-(ar)alkene, or
a nucleophile containing an $R^3$ group, in which $R^3$ is as defined;

the reagent in the second reaction step being different from that applied in the first reaction step.

Using two (or more) equivalents of the reagents in a single step reaction results in the same substitution in the 2- and 8-position, as opposed to a two step process, by which it is possible to obtain a compound with two different substituents on these positions, depending on the substituents and reagents used in each step.

The starting compound of formula (II) employed by the process of the present invention may be obtained, for example, by reacting with bromine, in the presence of a base, a compound of the following formula (V):

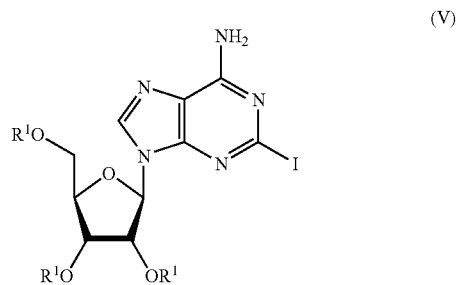

(V)

in which $R^1$ are the same or different and represent a hydrogen atom or a methylcarbonyl group. However, it should be clear that any other method of obtaining the starting compound is applicable in the method of the present invention.

The compounds obtained by the process of the invention are preferably those in which $R^2$ represents a halogen atom, a lower alkenyl or lower alkynyl and $R^3$ is an alkylamine, (ar)alkyl amine or alkynyl.

According to one embodiment, $R^2$ is iodine or a C$_6$-alkenyl or C$_6$-alkynyl group, the latter being respectively, in preference, 1-hexenyl or 1-hexynyl, the 1-hexenyl group being preferably the (E) 1-hexenyl isomer.

In case $R^3$ is an alkylamine group, it is preferably a lower alkylamine selected from the group consisting of methylamine, ethylamine, propylamine, butylamine, while in case $R^3$ is an (ar)alkylamine it is in preference benzylamine.

According to one embodiment, $R^2$ is 1-hexynyl. Yet, according to another embodiment, $R^2$ is (E)1-hexenyl. In both embodiments $R^3$ is preferably selected from methylamine, ethylamine, propylamine and butylamine.

The general process for the preparation of the C2,8-disubstituted adenosine derivatives 3–5, 7–23 is depicted in the following non-limiting scheme I:

SCHEME I

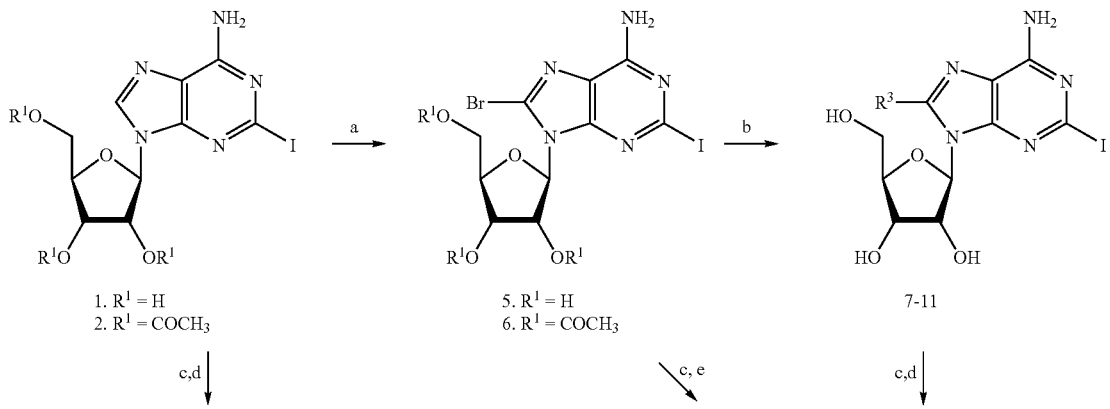

1. $R^1$ = H
2. $R^1$ = COCH$_3$

5. $R^1$ = H
6. $R^1$ = COCH$_3$ 7-11 c,d ↓   \c, e   c,d ↓

-continued

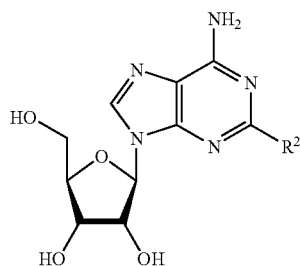

3. $R^2 = C\equiv C(CH_2)_3CH_3$
4. $R^2 = (E)\ HC=CH(CH_2)_3CH_3$

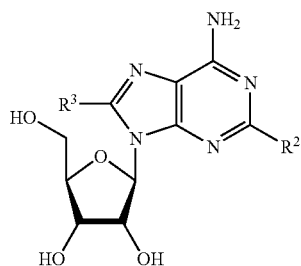

12-23

(a) (i) NaOAc buffer (1.0 M, pH 4), $Br_2$ (ii) $NaHSO_3$, aq. NaOH; (b) the appropriate amine; (c) $CH_3CN$, $Et_3N$, CuI, $PdCl_2$, $Ph_3P$ and 1-hexyn or (d) $CH_3CN$:DMF (1:1), tetrakis(triphenylphosphine)-palladium(0), $K_2CO_3$ and (E)-1-borocatechol)-1-hexene; (e) benzylamine, reflux;

As will be shown hereinafter, the compound 2-(1-Hexynyl)adenosine (3) was prepared (in good yield (85%)) by reacting 2-iodoadenosine (1) with 1-hexyn.[8,15] Compound 4 was prepared by reacting 1 with (E)-1-(borocatechol)-1-hexene.[10] To obtain the C2,8-disubstituted derivatives, either unprotected 2-iodoadenosine (1) or 2',3',5'-tri-O-acetyl-2-iodoadenosine (2) was brominated at the C8-position.[16]

Subsequently, different amines may be introduced at this position by stirring either 5 or 6 with the appropriate amine overnight. Under these reaction conditions the acetyl protecting groups, when present, were readily removed and compounds 7–11 were obtained (in good yields (70–91%)).

Finally, the 1-hexynyl and the (E)-1-hexenyl substituents were introduced at the 2-position as described above for compounds 3 and 4. Compounds 22 and 23 were obtained by treating 8-bromo-2-iodoadenosine (5) with an excess of either 1-hexyn or benzylamine.

According to another aspect, the present invention provides pharmaceutical compositions comprising as active ingredient a therapeutically effective amount, including a prophylactically effective amount, of one or more of the compounds of formula (I), or a salt of said compound, and a pharmaceutically acceptable additive. Preferred compounds employed in the compositions of the present invention are as defined above.

The term effective amount for the purposes described herein is that determined by such considerations as are known to those versed in the art. The amount must be sufficient to achieve a desired therapeutic effect, e.g. to treat a disease or a disorder. The effective amount is typically determined in appropriately designed clinical trials (e.g. dose range studies) and the person versed in the art will know how to properly conduct such trials in order to determine the effective amount. As generally known, an effective amount depends on a variety of factors including the affinity of the ligand to the receptor, its distribution profile within the body, a variety of pharmacological parameters such as half life in the body, on undesired side effects, if any, on factors such as age and gender, etc.

The pharmaceutical compositions of the invention are preferably for the treatment of diseases associated with the function of adenosine $A_{2A}$ receptor.

The term "treatment" as used herein refers to the administering of a therapeutic amount of the compound or composition of the present invention which is effective to ameliorate undesired symptoms associated with a disease, to prevent the manifestation of such symptoms before they occur, to slow down the progression of a disease, to slow down the deterioration of symptoms, to slow down the irreversible damage caused by the chronic stage of a disease, to lessen the severity or cure a disease, to improve survival rate or more rapid recovery, to prevent the disease from occurring, or a combination of two or more of the above. Treatment according to the invention preferably includes activation by one or more of the compounds of the present invention of an adenosine receptor (or elevation of an already active receptor) and preferably of the adenosine $A_{2A}$ receptor.

The term "pharmaceutically acceptable additives" used herein refers to any substance combined with said compound and include, without being limited thereto, diluents, excipients, carriers, solid or liquid fillers or encapsulating materials which are typically added to formulations to give them a form or consistency when it is given in a specific form, e.g. in pill form, as a simple syrup, aromatic powder, and other various elixirs. The additives may also be substances for providing the formulation with stability, sterility and isotonicity (e.g. antimicrobial preservatives, antioxidants, chelating agents and buffers), for preventing the action of microorganisms (e.g. antimicrobial and antifungal agents, such as parabens, chlorobutanol, phenol, sorbic acid and the like) or for providing the formulation with an edible flavor etc.

Preferably, the additives are inert, non-toxic materials, which do not react with the active ingredient of the invention. Yet, the additives may be designed to enhance the binding of the active agent to its receptor. Further, the term additive may also include adjuvants, being substances affecting the action of the active ingredient in a predictable way.

The additives can be any of those conventionally used and are limited only by chemico-physical considerations, such as solubility and lack of reactivity with the compound of the invention, and by the route of administration.

The active agent of the invention is preferably administered orally to the patient. Conventional methods such as administering the compound/s in tablets, suspensions, solutions, emulsions, capsules, powders, syrups and the like are usable.

For oral administration, the composition of the invention may contain additives for facilitating oral delivery of the compound/s of the invention. Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodiumk talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active agent in a flavor, usually sucrose and acacia or tragacanth, as well as pastilles comprising the active ingredient in an inert base, such as gelatin and glycerin, or sucrose and acacia, emulsions, gels, and the like. Such additives are known in the art.

Alternatively, the compound/s may be administered to the patient parenterally. In this case, the composition will generally be formulated in a unit dosage injectable form (solution, suspension, emulsion). Pharmaceutical formulation suitable for injection may include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, lipid polyethylene glycol and the like), suitable mixtures thereof and vegetable oils such as cottonseed oil, sesame oil, olive oil, soybean oil, corn oil, sunflower oil, or peanut oil; a fatty acid esters such as ethyl oleate and isopropyl myristate and variety of other solvent systems as known per se. The carrier may be chosen based on the physical and chemical properties of the active agent.

In case the active ingredient has a poor water solubility, and an oily carrier is therefore used proper fluidity can be maintained, for example, by the use of a coating such as lecithin, by the maintenance of the required particle size in the case of dispersion and by the use of surfactants.

Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations, in case the active ingredient has a poor water solubility, include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxy-ethylenepolypropylene copolymers, (d) amphoteric detergents such as, for example, alkyl-β-aminopriopionates, and 2-alkyl-imidazoline quaternary ammonium salts, and (3) mixtures thereof.

Further, in order to minimize or eliminate irritation at the site of injection, the compositions may contain one or more nonionic surfactants having a hydrophile-lipophile balance (HLB) of from about 12 to about 17. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The choice of an additive will be determined in part by the particular compound of the present invention, as well as by the particular method used to administer the composition.

Notwithstanding the above, the composition of the present invention may include one or more of the compounds of the present invention and may be comprise other biologically active substances, to provide a combined therapeutic effect.

As indicated hereinbefore, the compounds of the present invention were found to be capable of binding and activating or inducing the activity of adenosine receptors, particularly, of the adenosine $A_{2A}$ receptor. Accordingly, the composition of the present invention is preferably for the treatment of a disease or a disorder, which require for their treatment activation or induction of the activity of the adenosine $A_{2A}$ receptor present on a target cell. For example, the compound or composition of the present invention may be useful as therapeutic or prophylactic agents for circulatory diseases, such as hypertension and ischemic heart or brain disease. Also, the compounds or compositions of the present invention may be useful as neuroleptic agents, e.g. for the treatment of psychosis, or for wound healing.

The compounds and compositions of the present invention as set forth hereinabove and below are administered and dosed in accordance with good medical practice, taking into account the clinical conditions of the individual patient, the site and method of administration, scheduling of administration, individual's age, sex body weight and other factors known to medical practitioners.

The dose may be single daily dose or multiple doses over a period of several days. The treatment generally has a length proportional to the length of the disease process and drug effectiveness and the individual species being treated. Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments, until the optimum effect under the circumstances is reached. Exemplary dosages range from about 0.001 mg/kg body weight to about 10 mg/kg body weight of the subject being treated/day.

The invention has been described in an illustrative manner, and it is to be understood that the terminology, which has been used is intended to be in the is nature of words of description rather than of limitation. Obviously, many modifications and variations of the present invention are possible in light of the above teaching. It is therefore, to be understood that within the scope of the appended claims, the invention may be practiced otherwise than as specifically described hereinafter.

Throughout the description various publications are referred to by corresponding reference numbers. Full citations of the publications are listed hereinafter.

SPECIFIC EXAMPLES

Materials and Methods

Chemicals and Solvents All reagents were from standard commercial sources and of analytic grade. [$^3$H]DPCPX (1,3-dipropyl-8-cyclopentylxanthine), [$^3$H]CGS 21680 and [$^{125}$I]AB-MECA were purchased from NEN (Hoofddorp, The Netherlands).

Chromatography Thin-layer chromatography (TLC) was carried out using aluminum sheets (20×20 cm) with silica gel F$_{254}$ from Merck. Spots were visualized under UV (254 nm). Preparative column chromatography was performed on silica gel (230–400 mesh ASTM).

Instruments and Analyses. Elemental analyses were performed for C, H, N (Department of analytical Chemistry, Leiden University, The Netherlands). $^{13}$C NMR spectra were measured at 50.1 MHz with a JEOL JNM-FX 200 spectrometer equipped with a PG 200 computer operating in the Fourier-transform mode. $^1$H NMR spectra were measured at 200 MHz, using the above mentioned spectrometer, or at 300 MHz, using a Bruker WM-300 spectrometer equipped with an ASPECT-2000 computer operating in the Fourier-transform mode. Chemical shifts for $^1$H and $^{13}$C NMR are given in ppm (δ) relative to tetramethylsilane (TMS) as internal standard.

All high resolution mass spectra were measured on a Finnigan MAT900 mass spectrometer equipped with a direct insertion probe for EI experiments (70 eV with resolution 1000) or on a Finnigan MAT TSQ-70 spectrometer equipped with an electrospray interface for ESI experiments. Spectra were collected by constant infusion of the analyte dissolved in 80/20 methanol/H$_2$O. ESI is a soft ionization technique resulting in protonated, sodiated species in positive ionization mode and deprotonated species in the negative ionization mode.

Resolution of the compounds was achieved by reverse-phase HPLC (Gilson HPLC system, 712 system controller software. Gilson Netherlands, Meyvis en Co BV, Bergen op Zoom, the Netherlands) using as a mobile phase either: Eluent A: 20% CH$_3$CN in H$_2$O—100% CH$_3$CN in 35 minutes or Eluent B: 30% MeOH in H$_2$O—100% MeOH in 40 minutes; an Alltima C18 5μ (250 mm×4.6 mm) column (Alltech Nederland BV, Breda, the Netherlands) at a flow rate of 1 mL/min. The peaks were defined by measurement of UV absorbance (254 nm). Retention-times are given.

Melting points were determined in a Böchi capillary melting point apparatus.

Synthesis Procedures (In the following description the compounds are referred to at times by their number as defined in brackets after they first appear)

2-Iodoadenosine (compound 1) was prepared according to literature.[17] Yield 80%; mp 185–187÷C; Rf0.21 (10% MeOH in CH$_2$Cl$_2$).

2',3',5'-tri-O-Acetyl-2-iodoadenosine (Compound 2). To a suspension of 2-iodoadenosine (1, 400 mg, 1.02 mmol) and dimethylaminopyridine (DMAP, 9.32 mg, 0.08 mmol) in a mixture of acetonitrile (13 ml) and Et$_3$N (0.56 ml, 4.04 mmol) is added acid anhydride (0.34 ml, 3.60 mmol) at room temperature. After stirring for 1 hr the solution became clear. Methanol (5 ml) was added and stirring was continued for 5 min. The mixture was concentrated in vacuo. The residu was extracted with H$_2$O (15 ml) and EtOAc (15 ml). The organic layer was dried (MgSO$_4$), concentrated and purified further by column chromatography (eluens EtOAc). Yield 434 mg (0.84 mmol, 82%), R$_f$0.70 (10% MeOH in CH$_2$Cl$_2$); $^1$H NMR)(DMSO-d$_6$) δ 8.29 (s, 1H, H-8), 7.79 (bs, 2H, NH$_2$), 6.12 (d, 1H, J=5.15 Hz, H-1'), 5.84 (t, 1H, J=5.84 Hz, H-2'), 5.59 (t, 1H, J=5.14 Hz, H-3'), 4.40–4.25 (m, 3H, H-4',5'), 2.11 (s, 3H, COCH$_3$), 2.04 (s, 3H, COCH$_3$), 1.98 (s, 3H, COCH$_3$) ppm.

2-iodo-8-bromoadenosine (Compound 5). 2-Iodoadenosine (1, 2.93 g, 7.45 mmol) was dissolved in NaOAc buffer (1.0 M, pH 4, 50 ml) at 50° C. The solution was cooled to room temperature and bromine (0.46 mL, 8.94 mmol) was added. After stirring overnight at room temperature, adding NaHSO$_3$ destroyed the excess of bromine and the pH of the solution was adjusted to 7 with NaOH solution (5 M). The reaction mixture was kept at 4° C. for 5 hr and the precipitate was filtered. The white solid was washed with water and dried. Yield 2.43 mg (5.14 mmol, 69%), R$_f$ 0.69 (10% MeOH in EtOAc); $^1$H NMR (DMSO-d$_6$) δ 7.91 (s, 2H, NH$_2$), 5.77 (d, 1H, J=6.52 Hz, H-1'), 5.47 (d, 1H, J=5.84 Hz, OH-2'), 5.24 (d, 1H, J=4.80 Hz, OH-5'), 5.03–4.84 (m, 2H, OH-3', H-2'), 4.20–4.09 (m, 1H, H-3'), 3.97–3.88 (m, 1H, H-4'), 3.71–3.42 (m, 2H, H-5') ppm.

2',3',5'-tri-O-Acetyl-2-iodo-8-bromoadenosine (Compound 6). To an aqueous Na$_2$HPO$_4$ solution (10% w/v, 10 mL) was added bromine (83.5 μL). The mixture was stirred vigorously for 15 min. until most of the bromine had dissolved. Then 2.6 mL of the decanted bromine solution was added to 2',3',5'-tri-O-acetyl-2-iodoadenosine (2, 132 mg, 0.25 mmol) in dioxane (2.6 ml) cooled in an ice/water bath. After 20 min. the ice bath was removed and the reaction mixture was stirred overnight at room temperature. The mixture was cooled again (ice bath) and NaHSO$_3$ (1.8 M) was added dropwise until it became colorless. The water layer was extracted with CH$_2$Cl$_2$ (1×25 ml) and EtOAc (2×20 ml). The combined organic layers were dried (MgSO$_4$), filtered and concentrated in vacuo. The residue was purified by column chromatography (eluents EtOAc). Yield 94.2 mg (0.16 mmol, 63%), R$_f$ 0.61 (5% MeOH in CH$_2$Cl$_2$); $^1$H NMR (DMSO-d$_6$) δ 7.95 (bs, 2H, NH$_2$), 6.01–5.99 (m, 2H, H-1',2'), 5.75–5.73 (m, 1H, H-3'), 4.37–4.17 (m, 3H, H-4',5'), 2.10, 2.08, 1.97 (3×s, 9H, 3×COCH$_3$) ppm.

Amination of compound 5 or 6 to obtain the 8-alkylamino-2-iodoadenosines 7–10 was generally as follows: to 8-bromo-2-iodoadenosine (5) or 2',3',5'-tri-O-acetyl-2-iodo-bromoadenosine (6) (0.17 mmol) the appropriate alkylamine was added (excess) and the mixture was stirred overnight at room temperature. The reaction mixture was concentrated in vacuo and the product was crystallised from water.

2-Iodo-8-methylaminoadenosine (Compound 7). The reaction was performed with 2',3',5'-tri-O-acetyl-2-iodo-8-bromoadenosine (6, 100 mg, 0.17 mmol) and methylamine (16 ml, 40% w/v in water). Yield 54.6 mg (0.13 mmol, 77%), mp 162–164÷C; $^1$H NMR (DMSO-d$_6$) δ 7.02 (d, 1H, J=5.15 Hz, NH), 6.93 (s, 2H, NH$_2$), 5.77 (d, 1H, J=7.56 Hz, H-1'), 5.66 (t, 1H, J=4.81 Hz, OH-2'), 5.31 (d, 1H, J=6.52 Hz, OH-5'), 5.18 (d, 1H, J=4.46 Hz, OH-3'), 4.56 (q, 1H, J=5.15 Hz, H-2'), 4.09–4.04 (m, 1H, H-3'), 3.98–3.91 (m, 1H, H-4'), 3.68–3.57 (m, 2H, H-5'), 2.86 (d, 3H, J=4.46 Hz, CH$_3$); MS m/z 423 (M+H)$^+$; Anal. (C$_{11}$H$_{15}$IN$_6$O$_4$) C, H, N.

2-iodo-8-ethylaminoadenosine (Compound 8). The reaction was performed with 2-iodo-8-bromoadenosine (5, 90 mg, 0.19 mmol) and ethylamine (2.5 ml, 70% w/v in water). Yield 58.3 mg (0.13 mmol, 70%), mp 205–207÷C, R$_f$ 0.15 (10% MeOH in CH$_2$Cl$_2$); $^1$H NMR (DMSO-d$_6$) δ 6.97 (t, 1H, J=5.15 Hz, NH), 6.89 (s, 2H, NH$_2$), 5.79 (d, 1H, J=7.56 Hz, H-1'), 5.65–5.61 (m, 1H, OH-2'), 5.30 (d, 1H, J=6.18 Hz, OH-5'), 5.18 (d, 1H, J=3.77 Hz, OH-3'), 4.55 (q, 1H, J=6.17 Hz, H-2'), 4.08–4.04 (m, 1H, H-3'), 3.94 (bs, 1H, H-4'), 3.65–3.61 (m, 2H, H-5'), 2.49 (m, 2H, CH$_2$), 1.16 (t, 3H, J=7.21 Hz, CH$_3$); MS m/z 437 (M+H)$^+$; Anal. (C$_{12}$H$_{17}$IN$_6$O$_4$) C, H, N.

2-Iodo-8-propylaminoadenosine (Compound 9): The reaction was performed with 2-iodo-8-bromoadenosine (5, 90 mg, 0.19 mmol) and propylamine (2.5 ml, 70% w/v in water). Yield 68.8 mg (0.15 mmol, 80%), mp 160–162÷C, R$_f$ 0.20 (10% MeOH in CH$_2$Cl$_2$); $^1$H NMR (DMSO-d$_6$) δ 6.99 (t, 1H, J=4.80 Hz, NH), 6.87 (s, 2H, NH$_2$), 5.80 (d, 1H, J=8.24 Hz, H-1'), 5.67–5.63 (m, 1H, OH-2'), 5.30 (d, 1H, J=6.18 Hz, OH-5'), 5.18 (d, 1H, J=3.77 Hz, OH-3'), 4.56–4.51 (m, 1H, H-2'), 4.09–4.03 (m, 1H, H-3'), 3.96–3.94 (m, 1H, H-4'), 3.62–3.59 (m, 4H, H-5', NHCH$_2$), 1.57 (q, 2H, J=7.20 Hz, CH$_2$CH$_3$), 0.88 (t, 3H, J=7.50 Hz, CH$_3$); MS m/z 451 (M+H)$^+$; Anal. (C$_{13}$H$_{19}$IN$_6$O$_4$) C, H, N.

2-Iodo-8-butylaminoadenosine (Compound 10): The reaction was performed with 2-iodo-8-bromoadenosine (5, 1.15 g, 2.44 mmol) and n-butylamine (25 ml). Some drops of water were added to dissolve everything. Yield 0.92 g (1.98 mmol, 81%), mp 142–144÷C, R$_f$ 0.23 (10% MeOH in CH$_2$Cl$_2$); $^1$H NMR (DMSO-d$_6$) δ 6.94–6.86 (m, 3H, NH, NH$_2$), 5.79 (d, 1H, J=7.56 Hz, H-1'), 5.67–5.62 (m, 1H, OH-2'), 5.30–5.16 (m, 2H, OH-3',5'), 4.54–4.49 (m, 1H, H-2'), 4.07–4.04 (m, 1H, H-3'), 3.95–3.92 (m, 1H, H-4'), 3.64–3.57 (m, 2H, H-5'), 2.49–2.42 (m, 2H, NHCH$_2$), 1.55–1.26 (m, 4H, CH$_2$CH$_2$CH$_3$), 0.88 (t, 3H, J=7.21 Hz, CH$_3$); MS m/z 464 (M+H)$^+$; Anal. (C$_{14}$H$_{21}$IN$_6$O$_4$) C, H, N.

2-iodo-8-benzylaminoadenosine (Compound 11): 8-Bromo-2-iodoadenosine (5, 1.28 g, 2.14 mmol) was dissolved in benzylamine (21.4 mmol, 2.34 ml) and some drops of water were added to dissolve everything. The mixture was stirred overnight at 60° C. and concentrated in vacuo. The white solid was stirred in CH$_2$Cl$_2$, filtered and dried. Yield 0.97 g (1.95 mmol, 91%), mp 128–130÷C, R$_f$ 0.19 (5% MeOH in EtOAc); $^1$H NMR (DMSO-d$_6$) δ 7.65 (t, 1H, NH), 7.37–7.21 (m, 5H, phenyl), 6.91 (bs, 2H, NH$_2$), 5.86 (d, 1H, J=7.90 Hz, H-1'), 5.63 (t, 1H, J=3.43 Hz, OH-2'), 5.37 (d, 1H, J=6.52 Hz, OH-5'), 5.20 (d, 1H, J=3.77 Hz, OH-3'), 4.65–4.55 (m, 3H, H-2', NHCH$_2$), 4.12–4.07 (m, 1H, H-3'), 4.07–3.97 (m, 1H, H-4'), 3.64–3.61 (m, 2H, H-5'); MS m/z 498 (M+H)$^+$; Anal. (C$_{17}$H$_{19}$IN$_6$O$_4$) C, H, N.

The general procedure for the introduction of an 1-hexyn group at derivatives 1 and 7–11 to obtain compounds 3 and 12–16 is as follows: To a solution of 2-iodoadenosine (1) or the appropriate 2-iodo-8-(ar)alkylaminoadenosine (7–11) (0.65 mmol) in dry acetonitrile (5 ml) and Et$_3$N (5 ml) under an atmosphere of nitrogen were added CuI (9.3 mg, 48.8 μmol), PdCl$_2$ (6.0 mg, 33.8 μmol), Ph$_3$P (19.5 mg, 74.3 μmol) and 1-hexyn (3.15 mmol, 362 μl). The mixture was stirred overnight at room temperature under an atmosphere of nitrogen. The mixture was filtered, concentrated and purified by column chromatography.

2-(1-hexynyl)adenosine (Compound 3).[8] The reaction was performed with 2-iodoadenosine (1, 255 mg, 0.65 mmol) and 1-hexyn (3.15 mmol). The mixture was purified by column chromatography (5% MeOH in CH$_2$Cl$_2$). Yield 192 mg (0.55 mmol, 85%), mp 106–109÷C; R$_f$ 0.10 (10% MeOH in CH$_2$Cl$_2$); $^1$H NMR (DMSO-d$_6$) δ 8.37 (s, 1H, H-8), 7.41 (bs, 2H, NH$_2$), 5.84 (d, J=6.18 Hz, 1H, H-1'), 5.45 (d, J=6.18 Hz, 1H, OH-2'), 5.22–5.16 (m, 1H, OH-5'), 5.22–5.16 (m, 1H, OH-3'), 4.52 (q, J=5.15 Hz, 1H, H-2'), 4.11 (q, J=3.43 Hz, 1H, H-3'), 3.93 (pd, J=3.43 Hz, 1H, H4'), 3.65–3.48 (m, 2H, H-5'), 2.39 (t, J=6.86 Hz, 2H, ≡CCH$_2$), 1.51–1.39 (m, 4H, CH$_2$CH$_2$), 0.90 (t, 3H, J=6.87 Hz, CH$_3$); MS m/z 348 (M+H)$^+$; Anal. (C$_{16}$H$_{21}$N$_5$O$_4$ 0.22 CH$_2$Cl$_2$) C, H, N.

2-(1-Hexynyl)-8-methylaminoadenosine (Compound 12). The reaction was performed with 2-iodo-8-methylaminoadenosine (7, 50 mg, 0.12 mmol) and 1-hexyn (0.58 mmol). The mixture was purified by column chromatography (5% MeOH in CH$_2$Cl$_2$). Yield 36 mg (0.09 mmol, 79%), mp 161–163÷C; R$_f$ 0.23 (5% MeOH in CH$_2$Cl$_2$); $^1$H NMR (DMSO-d$_6$) δ 7.01 (d, 1H, J=4.81 Hz, NH), 6.61 (s, 2H, NH$_2$), 5.84 (d, 1H, J=7.55 Hz, H-1'), 5.78 (t, 1H, J=4.47 Hz, OH-2'), 5.26 (d, 1H, J=6.87 Hz, OH-5'), 5.15 (d, 1H, J=4.12 Hz, OH-3'), 4.58 (q, 1H, J=5.83 Hz, H-2'), 4.10–4.03 (m, 1H, H-3'), 3.95 (bs, 1H, H-4'), 3.62 (bs, 2H, H-5'), 2.87 (s, 3H, J=4.46 Hz, NHCH$_3$), 2.36 (t, 2H, J=6.87 Hz, ≡CCH$_2$), 1.53–1.39 (m, 4H, CH$_2$CH$_2$), 0.89 (t, 3H, J=6.87 Hz, CH$_3$); MS m/z 376 (M+H)$^+$; Anal. (C$_{17}$H$_{24}$N$_6$O$_4$) C, H, N.

2-(1-hexynyl)-8-ethylaminoadenosine (Compound 13). The reaction was performed with 2-iodo-8-ethylaminoadenosine (8, 67 mg, 0.15 mmol) and 1-hexyn (0.73 mmol). The mixture was purified by column chromatography (EtOAc-10% MeOH in EtOAc). Yield 49 mg (0.12 mmol, 83%), mp 230–232÷C; $^1$H NMR (DMSO-d$_6$) δ 6.97 (t, 1H, J=4.80 Hz, NH), 6.57 (s, 2H, NH$_2$), 5.86 (d, 1H, J=7.55 Hz, H-1'), 5.74 (t, 1H, J=4.80 Hz, OH-2'), 5.25 d, 1H, J=6.52 Hz, OH-5'), 5.15 (d, 1H, J=4.12 Hz, OH-3'), 4.57 (q, 1H, J=6.18 Hz, H-2'), 4.08 (m, 1H, H-3'), 3.95 (m, 1H, H4'), 3.64–3.60 (m, 2H, H-5'), 3.05 (m, 2H, NHCH$_2$), 2.36 (t, 2H, J=7.21 Hz, ≡CHCH$_2$), 1.51–1.40 (m, 4H, CH$_2$CH$_2$CH$_3$), 1.16 (t, 3H, J=7.20 Hz, NHCH$_2$CH$_3$), 0.89 (t, 3H, J=5.15 Hz, CH$_3$); MS m/z 391 (M+H)$^+$; Anal. (C$_{18}$H$_{26}$N$_6$O$_4$) C, H, N.

2-(1-Hexynyl)-8-propylaminoadenosine (Compound 14). The reaction was performed with 2-iodo-8-propylaminoadenosine (9, 68 mg, 0.15 mmol) and 1-hexyn (0.73 mmol). The mixture was purified by column chromatography (EtOAc-10% MeOH in EtOAc). Yield 49 mg (0.12 mmol, 80%), mp 184–186÷C; R$_f$ 0.60 (10% MeOH in EtOAc); $^1$H NMR (DMSO-d$_6$) δ 6.98 (t, 1H, J=5.15 Hz, NH), 6.54 (bs, 2H, NH$_2$), 5.87 (d, 1H, J=7.55 Hz, H-1'), 5.75 (t, 1H, J=4.46 Hz, OH-2'), 5.26 (d, 1H, J=6.86 Hz, OH-5'), 5.15 (d, 1H, J=4.12 Hz, OH-3'), 4.55 (q, 1H, J=6.86 Hz, H-2'), 4.06 (m, 1H, H-3'), 3.96 (bs, 1H, H4'), 3.61 (bs, 2H, H-5'), 2.49 (m, 2H, NHCH$_2$), 2.36 (m, 2H, ≡CCH$_2$), 1.60–1.42 (m, 6H, NHCH$_2$CH$_2$CH$_3$, CH$_2$CH$_2$), 0.89 (t, 6H, J=7.55 Hz, 2×CH$_3$); MS m/z 405 (M+H)$^+$; Anal. (C$_{19}$H$_{28}$N$_6$O$_4$) C, H, N.

2-(1-hexynyl)-8-butylaminoadenosine (Compound 15). The reaction was performed with 2-iodo-8-butylaminoadenosine (10, 200 mg, 0.43 mmol) and 1-hexyn (2.08 mmol). The mixture was purified by column chromatography (5% MeOH in CH$_2$Cl$_2$). Yield 111 mg (0.26 mmol, 62%), mp 182–184÷C; $^1$H NMR (DMSO-d$_6$) δ 6.95 (t, 1H, J=5.49 Hz, NH), 6.55 (bs, 2H, NH$_2$), 5.87 (d, 1H, J=7.90 Hz, H-1'), 5.77–5.72 (m, 1H, OH-2'), 5.26 (d, 1H, J=6.52 Hz, OH-5'), 5.15 (d, 1H, J=4.12 Hz, OH-3'), 4.54 (q, 1H, J=5.84 Hz, H-2'), 4.09–4.04 (m, 1H, H-3'), 3.95–3.93 (m, 1H, H-4'), 3.64–3.59 (m, 2H, H-5'), 3.09 (m, 2H, NHCH$_2$), 2.36 (m, 2H, ≡CCH$_2$), 1.51–1.30 (m, 8H, 2×CH$_2$CH$_2$), 0.89 (t, 6H, J=,7.55 Hz, 2×CH$_3$); MS m/z 419 (M+H)$^+$; Anal. (C$_{20}$H$_{30}$N$_6$O$_4$) C, H, N.

2-(1-hexynyl)-8-Benzylaminoadenosine (Compound 16). The reaction was performed with 2-iodo-8-benzylaminoadenosine (11, 230 mg, 0.46 mmol) and 1-hexyn (2.23 mmol). The mixture was purified by column chromatography (EtOAc). Yield 146 mg (0.32 mmol, 70%), mp 141–143÷C; R$_f$ 0.26 (5% MeOH in EtOAc); $^1$H NMR (DMSO-d$_6$) δ 7.64 (t, 1H, J=6.10 Hz, NH), 7.36–7.18 (m, 5H, phenyl), 6.59 (bs, 2H, NH$_2$), 5.92 (d, 1H, J=7.71 Hz, H-1'), 5.77 (t, 1H, J=4.85 Hz, OH-2'), 5.32 (d, 1H, J=6.74 Hz, OH-5'), 5.18 (d, 1H, J=4.18 Hz, OH-3'), 4.64 (q, 1H, J=4.64 Hz, H-2'), 4.58 (t, 2H, J=4.65 Hz, NHCH$_2$), 4.09 (t, 1H, J=4.09 Hz, H-3'), 3.98 (d, 1H, J=1.60 Hz, H-4'), 3.62 (q, 2H, J=2.58 Hz, H-5'), 2.36 (t, 2H, J=6.92 Hz, ≡CCH$_2$), 1.55–134 (m, 4H, CH$_2$CH$_2$), 0.89 (t, 3H, J=7.11 Hz, CH$_3$); MS m/z 453 (M+H)$^+$; Anal. (C$_{23}$H$_{28}$N$_6$O$_4$) C, H, N.

(E)-1-(borocatechol)-1-hexene.[10] Yield 75%; R$_f$ 0.28 (EtOAc:PE40/60 40/60=1:1).

General procedure for the introduction of an (E)-1-hexene group at derivatives 1 and 7–11 to obtain compounds 3 and 17–21 To a solution of 2-iodoadenosine (1) or the appropriate 2-iodo-8-(ar)alkylaminoadenosine (7–11) 0.82 mmol) in 20 ml of $CH_3CN:DMF$ (1:1) was added 50 mg of tetrakis(triphenylphosphine)palladium(0) and the mixture was stirred at room temperature for 15 min. Then 500 mg each of $K_2CO_3$ and (E)-1-borocatechol)-1-hexene (2.46 mmol) were added, and the suspension was refluxed for 5 hr. The mixture was filtered, concentrated in vacuo and purified by column chromatography.

2-((E)-1-hexenyl)adenosine (Compound 4).[10] The reaction was performed with 2-iodoadenosine (1, 150 mg, 0.38 mmol) and (E)-1-borocatechol)-1-hexene (1.14 mmol). The mixture was purified by column chromatography (5–30% MeOH in $CH_2Cl_2$). Yield 27 mg (0.08 mmol, 20%), mp 124–127÷C; $R_f$ 0.10 (10% MeOH in $CH_2Cl_2$); $^1H$ NMR (MeOD-$d_4$) δ 8.18 (s, 1H, H-8), 7.05–6.97 (m, 1H, =$CHCH_2$), 6.33 (d, 1H, J=15.44 Hz, =CH), 5.93 (d, 1H, J=6.52 Hz, H-1'), 4.81–4.78 (m, 1H, H-2'), 4.33 (d, 1H, J=4.81 Hz, H-3'), 4.17 (m, 1H, H-4'), 3.81 (dq, 2H, J=18.88 Hz, J=2.41 Hz, H-5'), 2.25 (q, 2H, J=5.84 Hz, =$CHCH_2$), 1.48–1.36 (m, 4H, $CH_2CH_2$), 0.93 (t, 3H, J=6.87 Hz, $CH_3$); MS m/z 350 (M+H)$^+$; HPLC, System A: 20–100% $CH_3CN$ in $H_2O$ in 35 min., retention time=8.92 min.; System B: 30–100% $CH_3OH$ in $H_2O$ in 40 min., retention time=20.37 min.

2-((E)-1-Hexenyl)-8-methylaminoadenosine (Compound 17). The reaction was performed with 2-iodo-8-methylaminoadenosine (7, 520 mg, 1.23 mmol) and (E)-1-borocatechol)-1-hexene (3.70 mmol). The mixture was purified by column chromatography (20% MeOH in $CH_2Cl_2$). Yield 42 mg (1.11 mmol, 9%), mp 161–166÷C; $R_f$ 0.60 (20% MeOH in $CH_2Cl_2$); $^1H$ NMR (MeOD-$d_4$) δ 6.91–6.83 (m, 1H, =$CHCH_2$), 6.29 (d, 1H, J=15.44 Hz, =CH), 5.98 (d, 1H, J=7.55 Hz, H-1'), 4.81–4.74 (m, 1H, H-2'), 4.29 (t, 1H, J=5.49 Hz, H-3'), 4.13 (m, 1H, H-4'), 3.82–3.79 (m, 2H, H-5'), 2.97 (m, 3H, $NHCH_3$), 2.29–2.22 (m, 2H, =$CHCH_2$), 1.52–1.36 (m, 4H, $CH_2CH_2$), 0.94 (t, 3H, J=6.52 Hz, $CH_3$); MS m/z 379 (M+H)$^+$; HPLC, System A: 20–100% $CH_3CN$ in $H_2O$ in 35 min., retention time=6.15 min.; System B: 30–100% $CH_3OH$ in $H_2O$ in 40 min., retention time=18.67 min.

2-((E)-1-hexenyl)-8-ethylaminoadenosine (Compound 18). The reaction was performed with 2-iodo-8-ethylaminoadenosine (8, 740 mg, 1.70 mmol) and (E)-1-borocatechol)-1-hexene (5.09 mmol). The mixture was purified by column chromatography (10–20% MeOH in $CH_2Cl_2$).Yield 23 mg (0.06 mmol, 5%), mp 128–130÷C; $R_f$ 0.61 (20% MeOH in $CH_2Cl_2$); $^1H$ NMR (MeOD-$d_4$) δ 6.92–6.82 (m, 1H, =$CHCH_2$), 6.29 (d, 1H, J=14.04 Hz, =CH), 6.02 (d, 1H, J =7.64 Hz<H-1'), 4.80–4.76 (m, 1H, H-2'), 4.29–4.27 (m, 1H, H-3'), 4.13–4.11 (m, 1H, H4'), 3.81 (q, 2H, J=10.89 Hz, H-5'), 3.42 (q, 2H, J=6.02 Hz, $NHCH_2$), 2.24 (q, 2H, J=6.00 Hz, =$CHCH_2$), 1.53–1.33 (m, 4H, $CH_2CH_2$), 1.28 (t, 3H, J=7.72 Hz, $NHCH_2CH_3$), 0.94 (t, 3H, J=7.11 Hz, $CH_3$); MS m/z 393 (M+H)$^+$; HPLC, System A: 20–100% $CH_3CN$ in $H_2O$ in 35 min., retention time=7.42 min.; System B: 30–100% $CH_3OH$ in $H_2O$ in 40 min., retention time=20.16 min.

2-((E)-1-hexenyl)-8-propylaminoadenosine (Compound 19). The reaction was performed with 2-iodo-8-propylaminoadenosine (9, 400 mg, 0.89 mmol) and (E)-1-borocatechol)-1-hexene (2.67 mmol). The mixture was purified by column chromatography (10% MeOH in $CH_2Cl_2$). Yield 43 mg (0.11 mmol, 12%), mp 170–172÷C; $R_f$ 0.41 (10% MeOH in $CH_2Cl_2$); $^1H$ NMR (MeOD-$d_4$) δ 6.93–6.82 (m, 1H, =$CHCH_2$), 6.29 (d, 1H, J=15.48 Hz, =CH), 6.04 (d, 1H, J=7.65 Hz, H-1'), 4.79–4.74 (m, 1H, H-2'), 4.29–4.26 (m, 1H, H-3'), 4.13–4.12 (m, 1H, H-4'), 3.81 (q, 2H, J=8.24 Hz, H-5'), 3.37–3.32 (m, 2H, $NHCH_2$), 2.24 (q, 21H, J=7.16 Hz, =$CHCH_2$), 1.89–1.66 (m, 2H, $NHCH_2CH_2$), 1.51–1.35 (m, 4H, $CH_2CH_2$), 1.02–0.91 (m, 6H, 2×$CH_3$); MS m/z 407 (M+H)$^+$; HPLC, System A: 20–100% $CH_3CN$ in $H_2O$ in 35 min., retention time=8.10 min.; System B: 30–100% $CH_3OH$ in $H_2O$ in 40 min., retention time=20.25 min.

2-((E)-1-hexenyl)-8-butylaminoadenosine (Compound 20). The reaction was performed with 2-iodo-8-butylaminoadenosine (10, 380 mg, 0.82 mmol) and (E)-1-borocatechol)-1-hexene (2.46 mmol). The mixture was purified by column chromatography (10% MeOH in $CH_2Cl_2$). Yield 42 mg (0.10 mmol, 12%); $R_f$ 0.44 (10% MeOH in $CH_2Cl_2$); $^1H$ NMR (MeOD-$d_4$) δ 6.94–6.80 (m, 1H, =$CHCH_2$), 6.28 (d, 1H, J=15.42 Hz, =CH), 6.02 (d, 1H, J=7.62 Hz, H-1'), 4.81–4.69 (m, 1H, H-2'), 4.31–4.20 (m, 1H, H-3'), 4.20–4.05 (m, 1H, H-4'), 3.87–3.70 (m, 2H, H-5'), 3.35–3.23 (m, 2H, $NHCH_2$), 2.29–2.05 (m, 2H, =$CHCH_2$), 1.72–1.20 (m, 8H, 2×$CH_2CH_2$), 1.00–0.83 (m, 6H, 2×$CH_3$); MS m/z 422 (M+H)$^+$; HPLC, System A: 20–100% $CH_3CN$ in $H_2O$ in 35 min., retention time=8.53 min.; System B: 30–100% $CH_3OH$ in $H_2O$ in 40 min., retention time=20.47 min.

2-((E)-1-hexenyl)-8-benzylaminoadenosine (Compound 21). The reaction was performed with 2-iodo-8-benzylaminoadenosine (11, 410 mg, 0.82 mmol) and (E)-1-borocatechol)-1-hexene (2.47 mmol). The mixture was purified by column chromatography (10% MeOH in $CH_2Cl_2$). Yield 41 mg (0.10 mmol, 11%), mp 153–155÷C; $^1H$ NMR (MeOD-$d_4$) δ 7.64 (t, 1H, J=6.10 Hz, NH), 7.36–7.18 (m, 5H, phenyl), 6.59 (bs, 2H, $NH_2$), 6.94–6.80 (m, 1H, =$CHCH_2$), 6.28 (d, 1H, J=15.42 Hz, =CH), 5.92 (d, 1H, J=7.71 Hz, H-1'), 5.77 (t, 1H, J=4.85 Hz, OH-2'), 5.32 (d, 1H, J=6.74 Hz, OH-5'), 5.18 (d, 1H, J=4.18 Hz, OH-3'), 4.64 (q, 1H, J=4.64 Hz, H-2'), 4.58 (t, 2H, J=4.65 Hz, $NHCH_2$), 4.09 (t, 1H, J=4.09 Hz, H-3'), 3.98 (d, 1H, J=1.60 Hz, H-4'), 3.62 (q, 2H, J=2.58 Hz, H-5'), 2.29–2.05 (m, 2H, =$CHCH_2$), 1.72–1.20 (m, 4H, $CH_2CH_2$), 1.00–0.83 (m, 3H, $CH_3$) ppm; MS m/z 456 (M+H)$^+$; HPLC, System A: 20–100% $CH_3CN$ in $H_2O$ in 35 min., retention time=9.61 min.; System B: 30–100% $CH_3OH$ in $H_2O$ in 40 min., retention time=26.10 min.

2,8di-(1-Hexynyl)adenosine (Compound 22). 2-iodo-8-bromoadenosine (5, 150 mg, 0.32 mmol) was dissolved in 3 mL $CH_3CN$ and 3 ml $Et_3N$ (dry). Then 4.5 mg CuI (23.6 μmol), 2.9 mg $PdCl_2$ (16.4 μmol) and 9.6 mg $Ph_3P$ (36.4 μmol) were added. Subsequently, 1.55 mmol (178 μl) 1-hexyn was added and the mixture was stirred under nitrogen atmosphere at room temperature overnight. The mixture was concentrated and purified by column chromatography (10% MeOH in $CH_2Cl_2$). Yield 96 mg (0.22 mmol, 70%), mp 146–148÷C; $R_f$ 0.48 (10% MeOH in $CH_2Cl_2$); $^1H$ NMR (MeOD-$d_4$) δ 7.61 (bs, 2H, $NH_2$), 5.89 (d, 1H, J=6.86 Hz, H-1'), 5.39 (d, 1H, J=6.18 Hz, OH-2'), 5.29–5.22 (m, 1H, OH-5'), 5.16 (d, 1H, J=4.12 Hz, OH-3'), 4.94 (q, 1H, J=5.83 Hz, H-2'), 4.15–4.13 (m, 1H, H-3'), 3.94–3.92 (m, 1H, H-4'), 3.72–3.44 (m, 2H, H-5'), 2.56 (t, 2H, J=6.52 Hz, ≡$CCH_2$), 2.44–2.34 (m, 2H, ≡$CCH_2$), 1.57–1.37 (m, 8H, $CH_2CH_2$), 0.93–0.86 (m, 6H, $CH_3$) ppm; MS m/z 429 (M+H)$^+$; Anal. ($C_{22}H_{29}N_5O_4$) C, H, N.

2,8-di-benzylaminoadenosine (Compound 23). 8-Bromo-2-iodoadenosine (5, 1.4 g, 2.34 mmol) was dissolved in benzylamine (23.4 mmol, 2.56 ml ) The mixture was heated at 140 C for 2 h. and was poured into $CHCl_3$. A precipitate was formed which was removed by filtration. The filtrate was concentrated and purified by column chromatography (0–10% MeOH in EtOAc). Yield 838 mg (1.76 mmol, 75%), mp 133–135÷C; $R_f$ 0.24 (5% MeOH in EtOAc); $^1H$ NMR (MeOD-$d_4$) δ 7.32–6.91 (m, 11H, 2×phenyl, NH), 6.35–6.29

(m, 1H, NH), 6.05 (bs, 2H, NH$_2$), 5.81 (d, 1H, J=6.86 Hz, H-1'), 5.66–5.54 (m, 1H, OH-2'), 5.20 (d, 1H, J=6.18 Hz, OH-5'), 5.04 (d, 1H, J=4.80 Hz, OH3'), 4.75–4.62 (m, 1H, H-2'), 4.56–4.38 (m, 4H, 2×CH$_2$), 4.13–4.04 (m, 1H, H-3'), 3.92–3.84 (m, 1H, H-4'), 3.65–3.52 (m, 2H, H-5') ppm; MS m/z 479 (M+H)$^+$; Anal. (C$_{24}$H$_{27}$N$_7$O$_4$) C, H, N.

The elemental analysis for compounds 1, 3, 7–17, 22 and 23 is provided in the following Table 1:

TABLE 1

Elemental Analysis

| No | Mol. Formula | Atom Calculated | Determined |
|---|---|---|---|
| 1 | C$_{10}$H$_{12}$IN$_5$O$_4$·0.33 C$_2$H$_5$CO$_2$C$_2$H$_5$ | C 32.18% | C 32.48% |
|  |  | H 3.49% | H 3.10% |
|  |  | N 16.60% | N 16.72% |
| 3 | C$_{16}$H$_{21}$N$_5$O$_4$·0.22 CH$_2$Cl$_2$ | C 53.25% | C 53.31% |
|  |  | H 5.91% | H 5.82% |
|  |  | N 19.15% | N 19.05% |
| 7 | C$_{11}$H$_{15}$IN$_6$O$_4$·1.9 H$_2$O | C 29.00% | C 29.19% |
|  |  | H 4.14% | H 4.21% |
|  |  | N 18.44% | N 18.18% |
| 8 | C$_{12}$H$_{17}$IN$_6$O$_4$·1.2 CH$_3$OH | C 33.41% | C 33.11% |
|  |  | H 4.64% | H 4.91% |
|  |  | N 17.68% | N 17.72% |
| 9 | C$_{13}$H$_{19}$IN$_6$O$_4$·1.8 HCON(CH$_3$)$_2$ | C 38.04% | C 37.95% |
|  |  | H 5.49% | H 5.71% |
|  |  | N 18.78% | N 18.80% |
| 10 | C$_{14}$H$_{21}$IN$_6$O$_4$ | C 36.22% | C 36.55% |
|  |  | H 4.56% | H 4.24% |
|  |  | N 18.10% | N 18.22% |
| 11 | C$_{17}$H$_{19}$IN$_6$O$_4$ | C 40.98% | C 40.59% |
|  |  | H 3.84% | H 4.05% |
|  |  | N 16.87% | N 16.50% |
| 12 | C$_{17}$H$_{24}$N$_6$O$_4$·2.9 H$_2$O | C 47.69% | C 47.66% |
|  |  | H 7.00% | H 7.21% |
|  |  | N 19.63% | N 19.73% |
| 13 | C$_{18}$H$_{26}$N$_6$O$_4$·0.5 H$_2$O | C 54.21% | C 54.10% |
|  |  | H 6.81% | H 7.01% |
|  |  | N 21.07% | N 21.4% |
| 14 | C$_{19}$H$_{28}$N$_6$O$_4$·1.6 H$_2$O | C 52.63% | C 52.70% |
|  |  | H 7.26% | H 7.23% |
|  |  | N 19.38% | N 19.19% |
| 15 | C$_{20}$H$_{30}$N$_6$O$_4$·1.4 H$_2$O | C 54.16% | C 54.11% |
|  |  | H 7.45% | H 7.72% |
|  |  | N 18.95% | N 19.14% |
| 16 | C$_{23}$H$_{28}$N$_6$O$_4$·1.0 H$_2$O | C 59.43% | C 59.39% |
|  |  | H 6.71% | H 6.69% |
|  |  | N 18.65% | N 18.28% |
| 22 | C$_{22}$H$_{29}$N$_5$O$_4$·0.8 HCON(CH$_3$)$_2$ | C 60.27% | C 60.10% |
|  |  | H 7.18% | H 7.00% |
|  |  | N 16.72% | N 16.46% |
| 23 | C$_{24}$H$_{27}$N$_7$O$_4$ | C 60.37% | C 60.65% |
|  |  | H 5.70% | H 5.37% |
|  |  | N 20.53% | N 20.44% |

Radioligand Binding Studies

Measurements with [$^3$H]DPCPX in the absence of GTP were performed according to a protocol published previously.[30] Adenosine A$_{2A}$ receptor affinities were determined according to Gao et al.[31] Adenosine A$_3$ receptor affinities were determined essentially as described.[28,29] Briefly, assays were performed in 50/10/1 buffer (50 mM Tris/10 mM MgCl$_2$/1 mM ethylenediaminetetra-acetic acid (EDTA) and 0.01% 3-([3-cholamidopropyl]-dimethylammonio)-1-propanesulfonate (CHAPS)) in glass tubes and contained 50 µl of a HEK 293 cell membrane suspension (10–30 µg), 25 µL [$^{125}$I]AB MECA (final concentration 0.15 nM), and 25 µl of ligand. Incubations were carried out for 1 hr at 37° C. and were terminated by rapid filtration over Whatman GF/B filters, using a Brandell cell harvester (Brandell, Gaithersburg, Md.). Tubes were washed three times with 3 ml of buffer. Radioactivity was determined in a Beckman 5500B γ-counter. Nonspecific binding was determined in the presence of 10$^{-5}$ M R-PIA.

cAMP assay. A$_{2A}$

CHO cells expressing the human adenosine A$_{2A}$ receptors were grown overnight as a monolayer in 24 wells tissue culture plates (400 µl/well; 2×10$^5$ cells/well). cAMP generation was performed in Dulbecco's Modified Eagles Medium (DMEM)/N-2-hydroxyethylpiperazin-N'-2-ethansulfonic acid HEPES) buffer (0.60 g HEPES/50 ml DMEM pH 7.4). To each well, washed three times with DMEM/HEPES buffer (250 µl), 100 µl DMEM/HEPES buffer, 100 µl adenosine deaminase (final concentration 5 IU/ml) and 100 µl of a mixture of rolipram and cilostamide (final concentration 50 µM each) were added. After incubation for 40 minutes at 37° C., 100 µL agonist was added. After 15 minutes at 37° C., the reaction was terminated by removing the medium and adding 200 µl 0.1 M HCl. Wells were stored at −20° C. until assay.

The amounts of cAMP were determined after a protocol with cAMP binding protein[12] with the following minor modifications. As a buffer was used 150 mM K$_2$HPO$_4$/10 mM EDTA/0.2% Bovine Serum Albumine (BSA) at pH 7.5. Samples (20 µl+30 µl 0.1 M HCl) were incubated for at least 2.5 hours at 0° C. before filtration over Whatman GF/B filters. Filters were additionally rinsed with 2×2 ml TrisHCl buffer (pH 7.4, 4° C.). Filters were counted in Packard Emulsifier Safe scintillation fluid (3.5 ml) after 24 hours of extraction.

Biological Evaluation

All compounds prepared were tested in radioligand binding assays to determine their affinities for the adenosine A$_1$ receptor in rat brain cortex, the A$_{2A}$ receptor in rat striatum and the human A$_3$ receptor as expressed in HEK 293 cells (Table 2, hereinafter). The K$_i$ values were computed from the displacement curves obtained by nonlinear regression of the competition curves with the software package Prism (Graph Pad, San Diego, Calif.)

For the adenosine A$_1$ receptor, the tritiated antagonist, [$^3$H]-1,3-dipropyl-8-cyclopentylxanthine ([$^3$H]DPCPX), and for the adenosine A$_{2A}$ receptor, the tritiated antagonist [$^3$H]ZM 241385 were used. Since radiolabeled antagonists are not commercially available for the adenosine A3 receptor, [125I]AB-MECA, an A3 receptor agonist, was used. Displacement experiments were performed in the absence of GTP.

All compounds prepared were also tested in a functional assay. The ability of the compounds (3–5, 7–23) to produce cAMP by activation of human adenosine A$_{2A}$ receptors expressed in CHO cells was assessed and compared to the reference full agonist CGS21680 (100%).

Results and Discussion

Compounds 3 and 4 were synthesized starting from the important intermediate 2-iodoadenosine (1).[17] The 2-(1-hexynyl) substituent was successfully introduced via a slightly modified traditional palladium-catalyzed cross-coupling reaction.[8] Synthesis of 2-alkenyl derivatives by the reaction of 1 with terminal alkenes in this classical cross-coupling have been shown to be disappointing, with E derivatives obtained in very low yields only.[10] An alternative route has been the preparation of a (E)-1-(borocatechol)-1-alkene complexe, by letting catecholborane react with the appropriate terminal alkyn. These (E)-1-(borocatechol)-1-alkene complexes have been coupled successfully with 2-iodoadenosine derivatives.[10] Treatment of 1, under similar conditions, with (E)-1-(borocatechol)-1-hexene, gave compound 4 in reasonable yield.

For the synthesis of the C2,8-disubstituted derivatives 12–23, 2-iodoadenosine (1) was brominated at the 8-position prior to the introduction of the 2-substituent. Using a standard bromination procedure, e.g. stirring 2-iodoadenosine (1) or 2',3',5'-tri-O-acetyl-2-iodoadenosine (2) in dioxan and adding bromine water (in phosphate buffer, 10% w/v, pH ~7),[18] yielded the corresponding 8-bromo derivatives. With the use of a different buffer (NaOAc buffer, 1.0 M, pH=4), 2-iodoadenosine (1) readily dissolved (50÷C) and after addition of $Br_2$, stirring overnight and subsequent adjustment of the pH to 7, the 8-brominated compound (5) was obtained as a white solid that could easily be filtered.[16] Subsequent amination at the 8-position was straightforward by stirring compound 5 with the appropriate amine (less nucleophilic amines needed some heating), and compounds 7–11 were obtained in good yields (70–91%).19

The introduction of the 1-hexynyl or the (E)-1-hexenyl substituents at the 2-position was achieved as described for compound 1, and yielded the desired compounds 12–21. The alternative synthesis of compounds 12–21 by the introduction of the 2-substituent prior to the 8-substituent failed. In this case, compound 3 was indeed brominated at the 8-position, however, addition of bromine at the triple bond occurred as well. Finally, reacting compound 5 with an excess of either 1-hexyn or benzylamine yielded compounds 22 and 23.

Table 2 displays radioligand binding data for all synthesized C2,8-adenosine derivatives (final products 1, 3–5, 7–23). The affinities of the adenosine analogues at adenosine $A_1$, $A_{2A}$ and $A_3$ receptors is expressed as $K_i$ values (±SEM in nM, n=3) or percentage displacement (n=2, mean value) at 10 μM.

TABLE 2

$K_i$ (nM) or % displacement at $10^{-5}$ M

| No | $R^2$ | $R^3$ | $A_1{}^a$ | $A_{2A}{}^b$ | $A_3{}^c$ | $A_3/A_{2A}$ |
|---|---|---|---|---|---|---|
| 1 | I | H | 36.1% | 4200 ± 80 | 297 ± 17 | 0.07 |
| 3 | C≡C(CH$_2$)$_3$CH$_3$ | H | 63.7% | 6 ± 1 | 16.9 ± 4.1 | 2.78 |
| 4 | (E) CH=CH(CH$_2$)$_3$CH$_3$ | H | 53.1% | 26.2 ± 1.8 | 73.5 ± 7.7 | 2.78 |
| 5 | I | Br | 21.6% | 43.1% | 6.2% | — |
| 7 | I | NHCH$_3$ | 35.2% | 43.3% | 7310 ± 440 | — |
| 8 | I | NHCH$_2$CH$_3$ | 35.2% | 40.6% | 5110 ± 890 | — |
| 9 | I | NH(CH$_2$)$_2$CH$_3$ | 40.2% | 50.7% | 8670 ± 2000 | — |
| 10 | I | NH(CH$_2$)$_3$CH$_3$ | 28.2% | 3110 ± 1650 | 43.1% | — |
| 11 | I | NHCH$_2$C$_6$H$_5$ | 35.5% | 44.7% | 39.5% | — |
| 12 | C≡C(CH$_2$)$_3$CH$_3$ | NHCH$_3$ | 31.6% | 115 ± 8 | 5640 ± 780 | 49.0 |
| 13 | C≡C(CH$_2$)$_3$CH$_3$ | NHCH$_2$CH$_3$ | 30.9% | 253 ± 29 | 8830 ± 1230 | 34.9 |
| 14 | C≡C(CH$_2$)$_3$CH$_3$ | NH(CH$_2$)$_2$CH$_3$ | 47.6% | 82 ± 10 | 2160 ± 120 | 26.3 |
| 15 | C≡C(CH$_2$)$_3$CH$_3$ | NH(CH$_2$)$_3$CH$_3$ | 539 ± 380 | 149 ± 29 | 64.3% | — |
| 16 | C≡C(CH$_2$)$_3$CH$_3$ | NHCH$_2$C$_6$H$_5$ | 756 ± 483 | 35.4% | 7970 ± 610 | — |
| 17 | (E) CH=CH(CH$_2$)$_3$CH$_3$ | NHCH$_3$ | 17.9% | 663 ± 106 | 13440 ± 2130 | 20.3 |
| 18 | (E) CH=CH(CH$_2$)$_3$CH$_3$ | NHCH$_2$CH$_3$ | 30.0% | 1840 ± 300 | 17530 ± 2100 | 9.53 |
| 19 | (E) CH=CH(CH$_2$)$_3$CH$_3$ | NH(CH$_2$)$_2$CH$_3$ | 49.5% | 678 ± 25 | 14330 ± 2160 | 21.1 |
| 20 | (E) CH=CH(CH$_2$)$_3$CH$_3$ | NH(CH$_2$)$_3$CH$_3$ | 906 ± 264 | 580 ± 250 | 47.4% | — |
| 21 | (E) CH=CH(CH$_2$)$_3$CH$_3$ | NHCH$_2$C$_6$H$_5$ | 2110 ± 560 | 26.3% | 24.3% | — |
| 22 | C≡C(CH$_2$)$_3$CH$_3$ | C≡C(CH$_2$)$_3$CH$_3$ | 50.3% | 28.7% | 254 ± 34 | — |
| 23 | NHCH$_2$C$_6$H$_5$ | NHCH$_2$C$_6$H$_5$ | 50.2% | 11.6% | 54.1% | — |

[a]displacement of [$^3$H]DPCPX from rat cortical membranes
[b]displacement of [$^3$H]ZM241385 from rat striatal membranes;
[c]displacement of [$^{125}$I]AB-MECA from the human $A_3$ receptor expressed in HEK 293 cells.

From Table 2 it is clear that most synthesized compounds had low affinities for the adenosine $A_1$ and $A_3$ receptor. The affinities of the compounds for the adenosine $A_{2A}$ receptor were higher, depending on the 2-substituent present. The compounds with an 8-alkylamino group had lower adenosine $A_{2A}$ receptor affinities than the C8-unsubstituted derivatives 3 and 4. The introduction of either an (E)-1-hexenyl or a 1-hexynyl substituent at the 2-position of 8-alkylamino adenosine derivatives led to an increase in affinity for the adenosine $A_{2A}$ receptor, up to approx. 7- or 60-fold, respectively (Table 2). The compounds had adenosine $A_{2A}$ receptor affinities in the nanomolar range, with compound 14 having the highest $A_{2A}$ receptor affinity ($K_i$ value of 82 nM). The introduction of 8-substituents at adenosine decreases the affinity of the resulting compounds for the adenosine receptors compared to adenosine itself. 8-Alkylamino adenosine derivatives had adenosine $A_1$ and $A_{2A}$ receptor affinities in the μM range, without substantial preference for either receptor, whereas introduction of a cyclopentyl group at the $N^6$-position led to an increase in adenosine $A_1$ receptor affinity up to 23-fold.[14] The 2-(1-hexynyl) adenosine derivatives 12–16 generally had higher adenosine $A_{2A}$ receptor affinities than the 2-((E)-1-hexenyl)-substituted compounds 17–21, in line with the receptor affinities of compounds 3 and 4. Within both 2-substituted series. (12–16 and 17–21, Table 2), the 8-propylamino substituent seemed to be tolerated best on the adenosine $A_{2A}$ receptor. This is in contrast with the 2-unsubstituted derivatives, for which the 8-methylamino group appeared optimal for adenosine $A_{2A}$ receptor affinity.[12] In general, all compounds were more adenosine $A_{2A}$ receptor selective compared to the $A_1$ receptor or the $A_3$ receptor. Exceptions were compounds 16 and 21, containing the large benzylamino group at the 8-position. These compounds displayed higher adenosine $A_1$ receptor affinities compared to $A_{2A}$ and $A_3$, indicating that the adenosine $A_1$ receptor seemed best capable of accommodating this group. A 1-hexynyl group at the 8-position strongly decreased the $A_{2A}$ receptor affinity as well (compounds 3 and 22). The adenosine $A_3$ receptor seemed better able to accommodate the 1-hexynyl group (22) than the benzylamino group at the 8-position (16, 21). Finally, the adenosine $A_{2A}$ receptor affinity of compound 16, with a 1-hexynyl group at the 2-position, was higher than that of the 2-benzylamino-substituted derivative (23), also in line with receptor (functional) data on either 2-(1-hexynyl)-[8] or 2-benzylamino-substituted[20] derivatives. Other adenosine derivatives substituted at the 8-position have not displayed very high receptor affinities.[14] However, as shown herein, 8-alkylamino-substituted adenosine derivatives were obtained with affinities in the low micromolar (17–20) or even nanomolar range (12–15) for the adenosine $A_{2A}$ receptor. Although the adenosine $A_{2A}$ receptor affinity was somewhat decreased with the introduction of the 8-alkylamino groups, the $A_{2A}$ receptor selectivity compared to ($A_1$ and) $A_3$ was increased. Many 2-substituted adenosine derivatives have been described as potent ligands for the $A_{2A}$ receptor, although binding data for the adenosine $A_3$ receptor is often lacking.[8,10,21,-23] Some 2-alkynyl adenosine derivatives have been tested on the adenosine $A_3$ receptor.[24-26] These compounds, such as HENECA (2-(1-hexynyl)-5'-deoxy-5'-N-ethylcarboxamidoadenosine), had high affinity for the $A_3$ receptor, and were often more selective for the adenosine $A_3$ compared to the $A_{2A}$ receptor. The 8-methylamino (12) and 8-propylamino (14) derivatives of 2-(1-hexynyl)adenosine (3), of the present invention showed high $A_{2A}$ receptor affinities with $K_i$ values of 115 and 82 nM, respectively. Furthermore, the selectivity for the adenosine $A_{2A}$ receptor compared to $A_3$ was approx. 49- and 26-fold, respectively. Although the affinities of the 2-(1-hexenyl)adenosines were somewhat lower, the selectivity for the $A_{2A}$ receptor was also increased.

The nanomolar adenosine $A_{2A}$ receptor affinities of compounds 12–15, and the acceptable $A_{2A}$ receptor affinities of compounds 17–20, indicate that the (fairly large) size of the substituents is not the main determining factor for the affinities of these compounds. The 8-substituents may have an influence on the conformation of the ligand itself (by forcing the ribose ring into the syn conformation). The conformation of 8-bromoadenosine in the crystal structure is syn, suggested to cause the low affinity of this compound for the adenosine receptors.[27-29] The bulkiness of 8-alkylamino groups was initially thought to force the ribose ring into the Syn conformation as well. However, from the X-ray structure of 8-(cyclopentylamino)-$N^6$-ethyladenosine it became apparent that the anti conformation is compatible with 8-substitution.[14] The difference in energy between the syn and the anti conformation is often not very large, and a direct steric hindrance at the receptor binding site seems to be a more probable explanation. Furthermore, the electronic (hydrogen bond formation) and lipophilic characteristics of the 8-substituents influence receptor affinity too.[12]

The effect of the synthesized compounds in cAMP assays was also determined. Table 3 shows the percentage of cAMP production via the human adenosine $A_{2A}$ receptor expressed in CHO cells compared to a reference agonist CGS 21680 (10 μM) (n=2, mean value, both values in percentage). The results are displayed in the following Table 3:

TABLE 3

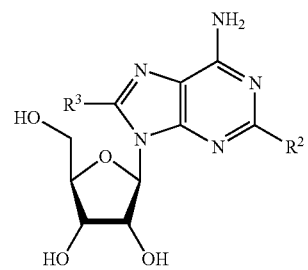

| No | $R^2$ | $R^3$ | % cAMP production $hA_{2A}$ |
|---|---|---|---|
| CGS 21680 | | | 100% |
| 1 | I | H | 126% (118–134) |
| 3 | C≡C(CH$_2$)$_3$CH$_3$ | H | 61% (58–64) |
| 4 | (E) CH=CH(CH$_2$)$_3$CH$_3$ | H | 82% (78–86) |
| 5 | I | Br | n.d. |
| 7 | I | NHCH$_3$ | 23% (20–25) |
| 8 | I | NHCH$_2$CH$_3$ | 77% (76–78) |
| 9 | I | NH(CH$_2$)$_2$CH$_3$ | 4% (3–5) |
| 10 | I | NH(CH$_2$)$_3$CH$_3$ | 28% (27–30) |
| 11 | I | NHCH$_2$C$_6$H$_5$ | 125% (92–157) |
| 12 | C≡C(CH$_2$)$_3$CH$_3$ | NHCH$_3$ | 85% (85–86) |
| 13 | C≡C(CH$_2$)$_3$CH$_3$ | NHCH$_2$CH$_3$ | 134% (124–143) |
| 14 | C≡C(CH$_2$)$_3$CH$_3$ | NH(CH$_2$)$_2$CH$_3$ | 58% (50–66) |
| 15 | C≡C(CH$_2$)$_3$CH$_3$ | NH(CH$_2$)$_3$CH$_3$ | 72% (63–82) |
| 16 | C≡C(CH$_2$)$_3$CH$_3$ | NHCH$_2$C$_6$H$_5$ | 83% (61–106) |

TABLE 3-continued

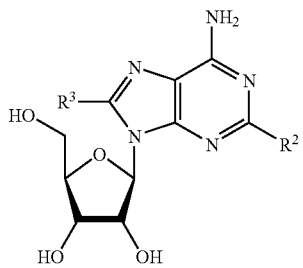

| No | R² | R³ | % cAMP production hA$_{2A}$ |
|---|---|---|---|
| 17 | (E) CH=CH(CH$_2$)$_3$CH$_3$ | NHCH$_3$ | 54% (49–59) |
| 18 | (E) CH=CH(CH$_2$)$_3$CH$_3$ | NHCH$_2$CH$_3$ | 65% (63–66) |
| 19 | (E) CH=CH(CH$_2$)$_3$CH$_3$ | NH(CH$_2$)$_2$CH$_3$ | 73% (70–76) |
| 20 | (E) CH=CH(CH$_2$)$_3$CH$_3$ | NH(CH$_2$)$_3$CH$_3$ | 36% (33–40) |
| 21 | (E) CH=CH(CH$_2$)$_3$CH$_3$ | NHCH$_2$C$_6$H$_5$ | 73% (72–75) |
| 22 | C≡C(CH$_2$)$_3$CH$_3$ | C≡C(CH$_2$)$_3$CH$_3$ | 99% (98–99) |
| 23 | NHCH$_2$C$_6$H$_5$ | NHCH$_2$C$_6$H$_5$ | 95% (90–100) |

For determination of the amount of cAMP produced via the adenosine A$_{2A}$ receptor, all compounds were first tested at a single concentration (approx. 100× the K$_i$ value). Compounds 3 and 4, without an alkylamino group at the 8-position, displayed partial agonism compared to the reference agonist CGS 21680. The intrinsic activity of compound 3 was less than that of compound 4. Compound 1, with iodine at the 2-position, behaved as a full agonist. Introduction of the 8-alkylamino groups to compound 1, led in most cases (except compound 11) to a decrease in intrinsic activity. Compound 9 showed a cAMP production of 4% only, compared to CGS 21680. Within the 2-(hexynyl) series (12–16), compounds 14–16 had similar intrinsic activities as the 8-unsubstituted compound 3, while 12 had a somewhat higher intrinsic activity. They all behaved as partial agonists compared to CGS 21680, whereas compound 13 behaved as a full agonist. Within the 2-(E)-alkenyl substituted series (17–21), the introduction of methyl-, ethyl-, and butylamino groups all decreased the intrinsic activity compared to compound 4. The intrinsic activities of compounds 19 and 21 were similar to that of 4 and they all behaved as partial agonists as well. Most compounds with very bulky C8-substituents (11, 16, 22 and 23) behaved as full agonists at the adenosine A$_{2A}$ receptor in this assay. Actually, GCS 21680 seemed a partial agonist here, since its intrinsic activity was lower than that of compounds 1, 11 and 13.

The C2,8-disubstituted adenosine derivatives disclosed herein were synthesized in good overall yields starting from 2-iodoadenosine. Most compounds appear to have adenosine A$_{2A}$ receptor affinities in the low micromolar or nanomolar range. Although the affinity for the adenosine A$_{2A}$ receptor was decreased somewhat with the introduction of the 8-alkylamino substituents, the selectivity for this receptor compared to the A$_3$ receptor was improved significantly. The 8-methylamino (12) and 8-propylamino (14). derivatives of 2-(1-hexynyl)adenosine (3), showed high A$_{2A}$ receptor affinities with K$_i$ values of 115 and 82 nM, respectively, and were 49- and 26-fold selective for the adenosine A$_{2A}$ receptor compared to the A$_3$ receptor. The adenosine A$_{2A}$ receptor seem to accommodate the 8-propyl- or 8-butylamino substituents best, whereas the even larger 8-substituents (8-benzylamino or 8-(1-hexynyl)) were not well tolerated. As for the intrinsic activity, the 8-unsubstituted compounds 3 and 4 displayed a reduced intrinsic activity compared to the reference agonist CGS21680. With the introduction of 8-alkylamino substituents the intrinsic activity was either not affected much, or as in most cases, was further reduced, and most of the compounds behaved as partial agonists. Most of the 8-substituted derivatives of 1 behaved as partial agonists as well.

LIST OF REFERENCES (1) Ralevic, V, Burnstock, G., *Pharmacol. Rev.*, 1998, 50, 413–491.

(2) Fink, J. S., Weaver, D .R., Rivkees, S. A., Peterfreund, R. A., Pollack, A. E., Adler, E. M., Reppert, S. M., *Mol. Brain Res.*, 1992, 14, 186–195.

(3) Ferrŕ, S., von Euler, G., Johansson, B., Fredholm, B.B., Fuxe, K , *Proc Natl. Acad. Sci. USA*. 7241–7238, 88, 1991.

(4) IJzerman, A. P., Van der Wenden, E. M., von Frijtag Drabbe Künzel, J. K., Mathôt, R. A. A., Danhof, M., Borea, P. A., Varani, K., *Nauntyn-Schmiedeberg's Arch. Pharmacol.*, 1994, 350, 638–645.

(5) Van Tilburg, E. W., Von Frijtag Drabbe Künzel, J., Groote, M., Vollinga, R. C., Lorenzen, A., IJzerman, A. P., N$^6$,5'-Disubstituted adenosine derivatives as partial agonists for the human adenosine A$_3$ receptor, *J. Med. Chem.*, 1999, 42, 1393–1400.

(6) Lorenzen, A., Sebastiao, A. M., Sellink, A., Vogt, H., Schwabe, U., Ribeiro, J. A., IJzerman, A. P., *Eur. J. Pharmacol.*, 1997, 334, 299–307.

(7) Van der Graaf, P. H., Van Schaick, E. A., Visser, S. A. G., De Greef, H. J. M. M., IJzerman, A. P., Danhof, M., *J. Pharmacol. Exp. Ther.*, 1999, 290, 702–709.

(8) Cristalli, G., Eleuteri, A., Vittori, S., Volpini, R, Lohse, M. J., Klotz, K.-N., *J. Med. Chem.*, 1992, 35, 2363–2368.

(9) Matsuda, A., Shinozald, M., Yamaguchi, T., Homma, H., Nomoto, R., Miyasaka, T., Watanabe, Y., Abiru, T., Nucleosides and nucleotides. 103. 2-Alkynyladenosines: *J. Med. Chem.*, 1992, 35, 241–252.

(10) Vittori, S., Camaioni, E., Di Francesco, E., Volpini, R., Monopoli, A., Dionisotti, S., Ongini, E., Cristalli, G, *J Med. Chem.*, 1996, 39, 4211–4217.

(11) Van der Wenden, E. M., Carnielli, M., Roelen, H. C. P. F., Lorenzen, A., von Frijtag Drabbe Künzel, J. K., IJzerman, A. P., *J. Med. Chem.*, 1998, 41, 102–108.

(12) Van der Wenden, E. M., Hartog-Witte, H. R., Roelen, H. C. P. F., Von Frijtag Drabbe Künzel, J. K., Pirovano, I. M., Maßth, R. A. A., Danhof, M., Van Aerschot, A., Lidaks, M. J., IJzerman, A. P., Soudijn, W., *Eur. J. Pharmacol-Mol. Pharmacol. Sect.*, 1995, 290, 189–199.

(13) van Schaick, E. A., Tukker, H. E., Roelen, H. C. P. F., IJzerman, A. P., Danhof, M., *Br. J. Pharmacol.*, 1998, 124, 607–618.

(14) Roelen, H., Veldman, N., Spek, A. L., von Frijtag Drabbe Künzel, J., Mathot, R. A., IJzerman, A. P., *J. Med. Chem.*, 1996, 39, 1463–1471.

(15) Matsuda, A., Shinozaki, M., Miyasaka, T., Machida, H., Abiru, T., *Chem. Pharm. Bull.*, 1985, 33, 1766–1769.

(16) Lin, T.-S., Cheng, J.-C., Ishiguro, K., Sartorelli, A. C., *J. Med. Chem.*, 1985, 28, 1481–1485.

(17) Robins, M. J., Uznanski, B., *Can. J. Chem.*, 1981, 59, 2601–2607.

(18) Ikehara, M., Uesugi, S., Kaneko, M., *J. Chem. Soc. Chem. Comm.*, 1967, 17–18.

(19) Chattopadyaya, J. B., Reese, C. B., *Synthesis*, 1977, 725.

(20) Francis, J. E., Webb, R. L., Ghai, G. R, Hutchison, A. J., Moskal, M. A., deJesus, R., Yokoyama, R., Rovinski, S. L., Contardo, N., Dotson, R., Barclay, B., Stone, G. A., Jarvis, M. F., *J. Med. Chem.*, 1991, 34, 2570–257.

(21) Keeling, S. E., Albinson, F. D., Ayres, B. E., Butchers, P. R., Chambers, C. L., Cherry, P. C. Ellis, F., Ewan, G. B., Gregson, M., Knight, J., Mills, K., Ravenscroft, P., Reynolds, L. H., Sanjar, S., Sheehan, M. *J. Bioorg. Med. Chem. Lett.*, 2000, 10, 403–406.

(22) Camaioni, E., DiFrancesco, E., Vittori, S., Volpini, R., Cristalli, G., *Bioorg. Med. Chem.*, 1997, 5, 2267–2275.

(23) Homma, H., Watanabe, Y., Abiru, T., Murayama, T., Nomura, Y., Matsuda, A., *J. Med. Chem.*, 1992, 35, 2881–2890.

(24) Vittori, S., Camaioni, E., Constanzi, S., Volpini, R., Klotz, K.-N., Cristalli, G., *Nucleosides and Nucleotides*, 1999, 18, 739–740.

(25) Volpini, R., Camaioni, E., Costanzi, S., Vittori, S., Klotz, K.-N., Cristalli, G., *Nucleosides and Nucleotides*, 1999, 18, 2511–2520.

(26) Klotz, K.-N., Camaioni, E., Volpini, R., Kachler, S., Vittori, S., Cristalli, G., *Naunyn-Schmiedeberg's Arch. Pharmacol.*, 1999, 360, 103–108.

(27) Bruns, R. F., *Can. J. Physiol. Pharmacol.*, 1980, 58, 673–690.

(28) Van Galen, P. J. M., Van Bergen, A. H., Gallo-Rodriquez, C., Melman, N., Olah, M. E., IJzerman, A. P., Stiles, G. L., Jacobson, K. A., *Mol. Pharmacol.*, 1994, 45, 1101–1111.

(29) Jacobson, K. A. In *Comprehensive Medicinal Chemistry, Volume* 3: Membranes & Receptors; Emmett, J. C., Ed.; Pergamon Press: Oxford, N.Y., 1990, p 601–642.

(30) Pirovano, I. M., IJzerman, A. P., Van Galen, P. J. M., Soudijn, W., *Eur. J. Pharmacol.*, 1989, 172, 185–193.

(31) Gao, Z.-G., IJzerman, A. P., *Biochem. Pharmacol.*, 2000, 60, 669–676.

(32) Olah, M. E., Gallo-Rodriquez, C., Jacobson, K. A., Stiles, G. L., *Mol. Pharmacol.*, 1994, 45, 978–982.

(33) Liu, G.-S., Downey, J. M., Cohen, M. V., Adenosine, ischemia, and preconditioning, In *Purinergic approaches in experimental therapeutics.* Jacobson, K. A., Jarvis, M. F., Ed.; Wiley-Liss, Inc: New York, 1997; pp 153–172.

What is claimed is:
1. A compound of the general formula (I):

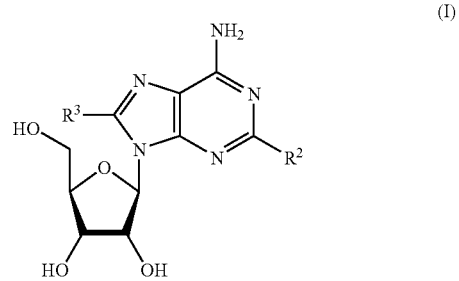

wherein
$R^2$ and $R^3$, which may be the same or different, represent a lower alkyl; a lower alkenyl; a lower alkynyl; a lower (ar)alkyl; a lower alkoxy; a lower alkylidenehydrazino; a cyano; an acetoamino; a halogen; a group of the general formula —$NR^4R^5$, wherein $R^4$ and $R^5$ represent, independently, a hydrogen atom, a lower alkyl or an (ar)alkyl group; or a group of the general formula —$SR^6$, wherein $R^6$ represents a hydrogen, a lower alkyl, a lower alkanoyl or an (ar)alkyl group;
or a salt of said compound, with the provisos that:
(i) when $R^2$ represents —$NH_2$, $R^3$ represents a lower alkenyl, a lower alkynyl, a lower (ar)alkyl, a lower alkylidenehydrazino, a cyano, an acetoamino, a group of the general formula —$NR^4R^5$; wherein one of —$R^4$ or $R^5$ represents, independently, a hydrogen atom; or wherein $R^4$ and $R^5$ represent, independently, -a lower alkyl or an (ar)alkyl group, or a group of the general formula —$SR^6$; wherein $R^6$ represents a hydrogen, a lower alkyl, a lower alkanoyl or an (ar)alkyl group;
(ii) when $R^2$ represents an alkylthio, $R^3$ does not represent an alkyl;
(iii) when $R^2$ represents a halogen or an alkyl, $R^3$ does not represent, respectively, a halogen or an alkyl.

2. The compound of claim 1, wherein $R^2$ is a halogen atom, an alkenyl group, an alkynyl group or an (ar) alkylamino group.

3. The compound of claim 2, wherein said halogen atom is iodine.

4. The compound of claim 2, wherein said alkenyl group or said alkynyl group is, respectively a $C_6$-alkenyl group or a $C_6$-alkynyl group.

5. The compound of claim 4, wherein said $R^2$ is 1-hexenyl or 1-hexynyl.

6. The compound of claim 5, wherein said 1-hexenyl is the (E)1-hexenyl isomer.

7. The compound of claim 1, wherein $R^3$ represents an alkylamino group, an (ar)alkylamino group or an alkynyl group.

8. The compound of claim 7, wherein said alkylamino group is selected from methylamino, ethylamino, propylamino, and butylamino; and said (ar)alkylamino group is a benzylamino group.

9. The compound of claim 1, wherein said $R^2$ is 1-hexynyl and $R^3$ is selected from a methylamino group, an ethylamino group, a propylamino group and a butylamino group.

10. The compound of claim 1, wherein said $R^2$ is (E)1-hexenyl and $R^3$ is selected from a methylamino group, a thylamino group, a propylamino group and a butylamino group.

11. The compound of claim 1, which is an adenosine $A_{2A}$ receptor agonist.

12. The compound of claim 1, which is a partial adenosine A2A receptor agonist.

13. The compound of claim 1, selected from the group consisting of the following compounds:
2-iodo-8-methyl aminoadenosine;
2-iodo-8-ethyl aminoadenosine;
2-iodo-8-propylaminoadenosine;
2-iodo-8-butylaminoadenosine;
2-iodo-8-benzylaminoadenosine;
2-(1-hexynyl)-8-methylaminoadenosine;
2-(1-hexynyl)-8-ethylaminoadenosine;
2-(1-hexynyl)-8-propylaminoadenosine;
2-(1-hexynyl)-8-butylaminoadenosine;
2-(1-hexynyl)-8-benzylaminoadenosine;
2-((E)-1-hexenyl)-8-methylaminoadenosine;
2-((E)-1-hexenyl)-8-ethylaminoadenosine;
2-((E)-1-hexenyl)-8-propylaminoadenosine;
2-((E)-1-hexenyl)-8-butylaminoadenosine;
2-((E)-1-hexenyl)-8-benzylaminoadenosine;
2,8-di-(1-hexynyl)adenosine; and
2,8-di-benzylaminoadenosine.

14. A pharmaceutical composition comprising as active ingredient an effective amount of a compound of the formula (I):

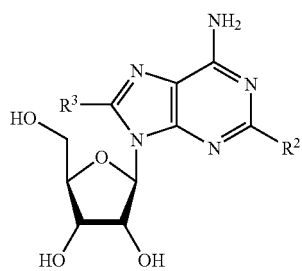

or a salt thereof,
wherein
$R^2$ and $R^3$ which may be the same or different, represent a lower alkyl; a lower alkenyl; a lower alkynyl; a lower (ar)alkyl; a lower alkoxy; a lower alkylidenehydrazino group-; a cyano; an acetoamino; a halogen; a group of the general formula —$NR^4R^5$ wherein $R^4$ and $R^5$ represent, independently, a hydrogen atom, a lower alkyl or an (ar)alkyl group; or a group of the general formula —$SR^6$, wherein $R^6$ represents a hydrogen, a lower alkyl, a lower alkanoyl or an (ar)alkyl group; with the provisos that
when $R^2$ represents —$NH_2$, $R^3$ does not represent a halogen, an alkyl or an alkoxy;
when $R^2$ represents an alkylthio, $R^3$ does not represent an alkyl;
when $R^2$ represents a halogen or an alkyl, $R^3$ does not represent, respectively, a halogen or an alkyl group;
and in combination with one or more pharmaceutically acceptable additives.

15. The pharmaceutical composition of claim 14, wherein $R^2$ is a halogen atom, an alkenyl group, an alkynyl group or an (ar)alkylamino group.

16. The pharmaceutical composition of claim 15, wherein said halogen atom is iodine.

17. The pharmaceutical composition of claim 15, wherein said alkenyl group or alkynyl group is a $C_6$-alkenyl group or a $C_6$-alkynyl group.

18. The pharmaceutical composition of claim 17, wherein said $R^2$ is 1-hexenyl or 1-hexynyl.

19. The pharmaceutical composition of claim 18, wherein said 1-hexenyl is the (E) 1-hexenyl isomer.

20. The pharmaceutical composition of claim 14, wherein $R^3$ represents an alkylamino group, an (ar)alkylamino group or an alkynyl group.

21. The pharmaceutical composition of claim 20, wherein said alkylamino group is selected from a methylamino group, an ethylamino group, a propylamino group, and a butylamino group, and wherein said (ar)alkylamino group is a benzylamino group.

22. The pharmaceutical composition of claim 14, wherein said $R^2$ is 1-hexynyl and $R^3$ is selected from a methylamino group, an ethylamino group, a propylamino group and a butylamino group.

23. The pharmaceutical composition of claim 14, wherein said $R^2$ is (E)1-hexenyl and $R^3$ is selected from a methylamino group, an ethylamino group, a propylamino group and a butylamino group.

24. A method for achieving activation of adenosine $A_{2A}$A receptor in a cell comprising administering to said cell the composition of claim 14.

25. A method according to claim 24, wherein said activation is partial activation.

* * * * *